United States Patent
Wang et al.

(10) Patent No.: US 10,413,268 B2
(45) Date of Patent: Sep. 17, 2019

(54) HYBRID IMAGING APPARATUS AND METHODS FOR INTERACTIVE PROCEDURES

(71) Applicant: Carestream Health, Inc., Rochester, NY (US)

(72) Inventors: Xiaohui Wang, Pittsford, NY (US); David H. Foos, Webster, NY (US); Michael D. Heath, Rochester, NY (US); Richard A. Simon, Rochester, NY (US); Eliot L. Siegel, Severna Park, MD (US)

(73) Assignee: Carestream Health, Inc., Rochester, NY (US)

( * ) Notice: Subject to any disclaimer, the term of this patent is extended or adjusted under 35 U.S.C. 154(b) by 565 days.

(21) Appl. No.: 15/054,493

(22) Filed: Feb. 26, 2016

(65) Prior Publication Data

US 2016/0256128 A1 Sep. 8, 2016

Related U.S. Application Data

(60) Provisional application No. 62/127,387, filed on Mar. 3, 2015.

(51) Int. Cl.
*A61B 6/00* (2006.01)
*H05G 1/54* (2006.01)
(Continued)

(52) U.S. Cl.
CPC ............... *A61B 6/54* (2013.01); *A61B 6/025* (2013.01); *A61B 6/4007* (2013.01);
(Continued)

(58) Field of Classification Search
CPC ......... A61B 6/022; A61B 6/502; A61B 6/025; A61B 6/027; A61B 6/12; A61B 6/481; A61B 6/487; A61B 6/488; A61B 6/504; A61B 6/032; A61B 6/06; A61B 6/08; A61B 6/482; A61B 6/486; A61B 6/04; A61B 6/547; A61B 5/055; A61B 6/4007; A61B 6/4233; A61B 6/4291; A61B 6/5282; A61B 6/0414; A61B 6/4405; A61B 6/54; A61B 6/541; A61B 6/4028; A61B 6/4035;
(Continued)

(56) References Cited

U.S. PATENT DOCUMENTS

| 5,943,388 A * | 8/1999 | Tumer ............... G01V 5/0041 378/98.11 |
| 7,505,562 B2 | 3/2009 | Dinca et al. |

(Continued)

FOREIGN PATENT DOCUMENTS

DE 10 2010 062541 6/2012

OTHER PUBLICATIONS

European Search Report, dated Nov. 22, 2016, European Application No. 16158534.4, 3 pages.
(Continued)

*Primary Examiner* — Irakli Kiknadze

(57) ABSTRACT

An imaging system includes an x-ray assembly having one or more x-ray sources configured to be energized at multiple positions. A control program energizes the one or more x-ray sources in a programmed sequence and controls the timing of the sequence.

21 Claims, 27 Drawing Sheets

(51) Int. Cl.
  *H01J 35/00*  (2006.01)
  *A61B 6/02*  (2006.01)
  *H01J 35/06*  (2006.01)
  *H01J 35/10*  (2006.01)
  *A61B 6/12*  (2006.01)

(52) U.S. Cl.
  CPC .......... *A61B 6/4405* (2013.01); *A61B 6/4452* (2013.01); *A61B 6/487* (2013.01); *A61B 6/488* (2013.01); *A61B 6/5205* (2013.01); *A61B 6/541* (2013.01); *H01J 35/06* (2013.01); *H01J 35/10* (2013.01); *A61B 6/027* (2013.01); *A61B 6/12* (2013.01); *A61B 6/481* (2013.01); *A61B 6/504* (2013.01)

(58) Field of Classification Search
  CPC ... A61B 6/4216; A61B 6/4225; A61B 6/4441; A61B 6/4447; A61B 6/4476; A61B 6/4241; A61B 6/5235; A61B 6/5252; A61B 6/4014; A61B 6/4071; A61B 6/4085; A61B 6/4458; A61B 6/4452; A61B 6/5205; H01J 35/06; H01J 35/10; H01J 1/3048; H01J 2235/081; H01J 1/15; H01J 1/16; H01J 35/08; H01J 35/065; H01J 35/30; H01J 2201/342; H01J 2235/068; H01J 35/32; H01J 2235/062; H01J 1/135; H01L 2227/326; H01L 27/3276; H01L 27/3279; H01L 51/5203; H01L 35/06; H01L 35/10; G01N 23/046; G01N 2223/419; G01N 2223/612; G01N 23/04; G01T 1/17; G01T 1/36; H05G 1/58
  USPC ..... 378/4, 9, 21, 42, 62, 116, 119, 193, 196, 378/197
  See application file for complete search history.

(56) References Cited

U.S. PATENT DOCUMENTS

| | | |
|---|---|---|
| 8,172,633 B2 | 5/2012 | Park et al. |
| 2006/0227131 A1 | 10/2006 | Schiwietz et al. |
| 2008/0118023 A1 | 5/2008 | Besson |
| 2011/0003109 A1 | 1/2011 | Slinker et al. |
| 2011/0216884 A1* | 9/2011 | Tsujii .................. A61B 6/06 378/62 |
| 2012/0134464 A1 | 5/2012 | Hoernig et al. |
| 2012/0195403 A1 | 8/2012 | Vedantham et al. |
| 2014/0093032 A1 | 4/2014 | Dennerlein |
| 2014/0153690 A1* | 6/2014 | Claus .................. A61B 6/025 378/9 |
| 2015/0043712 A1 | 2/2015 | Wang et al. |

OTHER PUBLICATIONS

European Search Report, dated Jul. 7, 2016, European Application No. 16158534.4, 2 pages.
M. Alhrishy et al., "Interventional Digital Tomosynthesis from a Standard Fluoroscopy System Using 2D-3D Registration", MIC-CAI 2013, Part III, LNCS 8151, 2013, pp. 98-105.

* cited by examiner

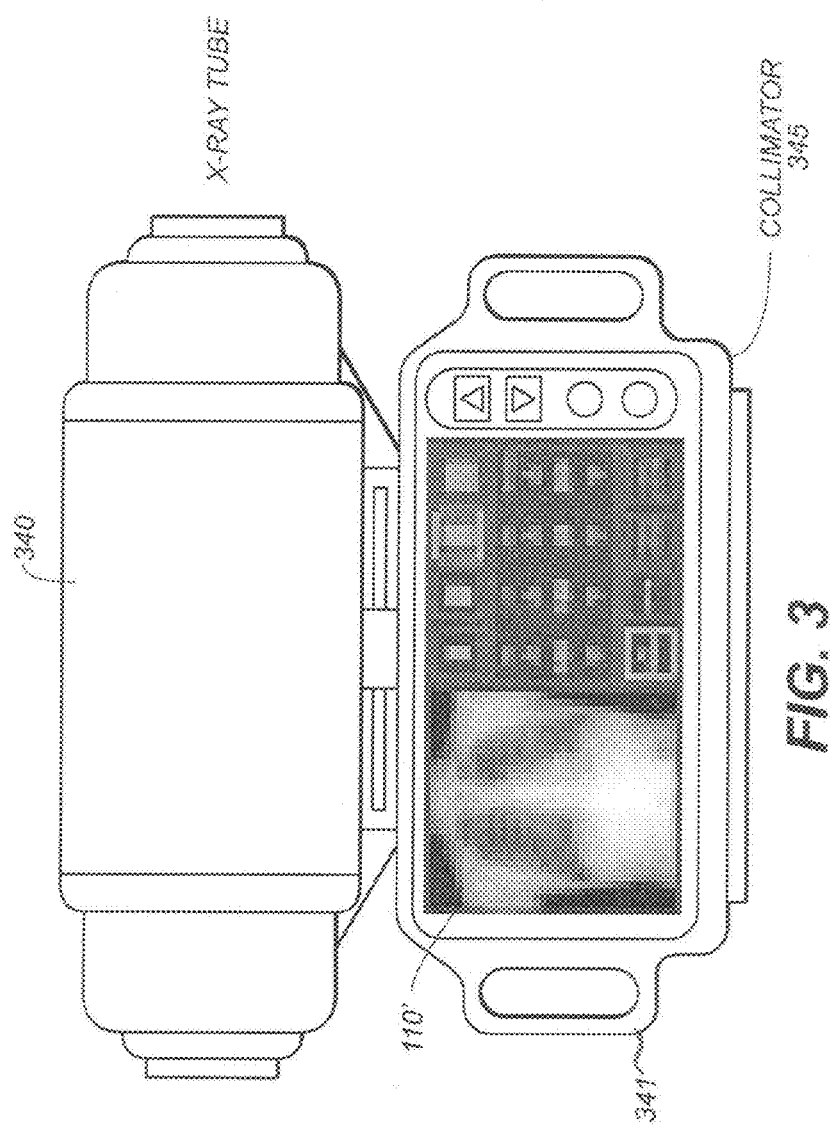

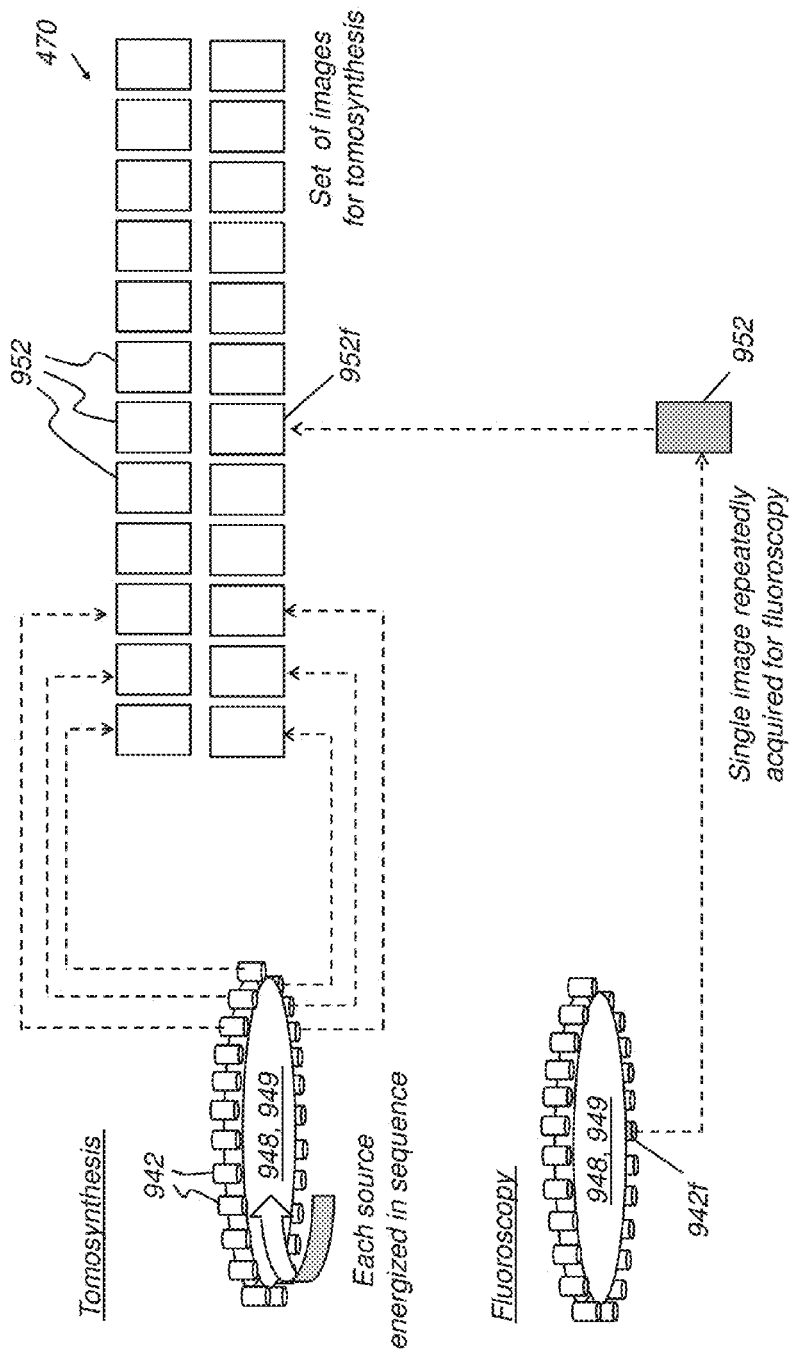

HYBRID IMAGING APPARATUS AND METHODS FOR INTERACTIVE PROCEDURES

CROSS-REFERENCE TO RELATED APPLICATIONS

This application claims priority to U.S. patent application Ser. No. 62/127,387, filed Mar. 3, 2015, in the name of Wang et al., and entitled HYBRID IMAGING METHODS FOR INTERACTIVE PROCEDURES.

This application is related in certain respects to U.S. patent application Ser. No. 14/190,447, filed Feb. 26, 2014, in the name of Wang et al., and entitled IMAGING SYSTEM AND METHOD FOR PORTABLE STEREOSCOPIC TOMOGRAPHY, which is incorporated herein by reference in its entirety.

TECHNICAL FIELD

The disclosure relates generally to the field of radiography and more particularly to apparatus and methods for adaptively generating and displaying images of different types to track progress of a procedure in multiple modalities from the same radiography system.

BACKGROUND

A wide range of invasive and exploratory medical procedures are performed with the aid of fluoroscopic imaging equipment for monitoring progress. Fluoroscopy provides "real-time" radiographic imaging that may be particularly useful for tracking motion that is related to a diagnostic procedure and is often used to monitor progress of an iodinated contrast agent or to help a practitioner in guiding a catheter through the veins of a patient in order to reach a location in the patient's body that requires some form of treatment, e.g., the site of a tumor or abscess.

The fluoroscopy-guided process of catheter placement and guidance requires considerable skill and often entails an amount of risk. Guidance procedures may be time consuming and may be difficult to execute, since the ability to visualize a catheter tip as it progressively advances through complex venous structures is inhibited by problems such as poor subject contrast, obstructed visibility, and dose constraints. Once a catheter is appropriately positioned, a treatment delivery device may be inserted through the catheter to the site of the abnormality and a treatment applied. For example, the treatment may involve embolization to cut off the blood supply that feeds a tumor, or to ablate a tumor using thermal methods, or, in the case of an abscess, to drain infectious material.

Conventionally, radiographic imaging to support state-of-the-art interventional procedures uses expensive, specialized C-arm systems that position the x-ray source and detector in a fixed position with respect to each other and allow a limited level of flexibility in placement of the source-detector pair about the object that is to be imaged. C-arm fluoroscopy systems are equipped with high frame rate flat panel detectors that provide two-dimensional (2-D) images. Supporting components for these imaging systems may include heads-up monitors, for example, that allow the practitioner to view the progress of an interventional procedure, such as catheter insertion or a surgical operation.

One limitation of conventional imaging systems used for fluoroscopy relates to the need for repositioning of C-arm components at various points during a procedure. Visibility of a catheter device or of contrast agent progress may be obscured at particular angles or positions so that adjustment of source and detector positioning is required in order to maintain useful tracking. In some cases, the needed movement of the C arm may interfere with the procedure or require that the practitioner shift position to allow C arm movement, which can be undesirable.

Another limitation of conventional imaging systems used for fluoroscopy relates to the lack of depth information. Systems dedicated solely to fluoroscopic imaging are optimized to show movement in real-time, but provide only 2-dimensional (2-D) images to the viewer. A separate tomography or other depth imaging apparatus must be used if depth information is to be obtained.

Tomography (also referred to as x-ray computed tomography or computed tomography (CT)) is a well known medical imaging method that uses computer processing to acquire and combine image data from multiple angles. In computed tomography, digital image processing is used to generate a three-dimensional image of the inside of an object from a series/collection of two-dimensional x-ray images taken around a single axis of rotation. In an idealized CT apparatus, a source/detector makes one or more complete 360-degree rotations about the subject obtaining a complete volume of data from which images may be reconstructed. The volume of data produced by the CT system is manipulated to generate depth images of various internal structures. The images may be generated in the axial or transverse plane (e.g., perpendicular to the long axis of the body), or reformatted in various planes, or volumetric three-dimensional representations.

Tomosynthesis combines digital image capture and processing with some portion of the source/detector motion used in tomography. While there are some similarities to CT, tomosynthesis has a number of differences from CT as conventionally practiced and is largely considered as a separate technique. As noted above, in CT, the source/detector makes a complete 360-degree rotation about the subject obtaining a complete set of data from which images may be reconstructed. By contrast, digital tomosynthesis uses a small rotation angle (e.g., 30 degrees) with a small number of discrete slices/exposures (e.g., 25-70 exposures). This set of data, incomplete with regard to full volume image information, is digitally processed to yield images similar to tomography but with a broader depth of field. Since the image is digitally generated and represented, various processing techniques may be used to generate and present a series of slices at different tissue depths and with different thicknesses reconstructed from the same image acquisition, thereby saving time and reducing radiation exposure.

Acquired tomosynthesis data may be incomplete in terms of the full three dimensions of data content. Tomosynthesis offers higher depth resolution in image slices parallel to a detector than CT offers, while CT may provide better isotropic resolution. Tomosynthesis is advantaged over 2-D radiography as it provides a measure of depth detail that is not otherwise available with conventional radiography. Moreover, the limited depth detail information that it offers can be of value to supplement fluoroscopic display. The resulting depth display provides improved visualization over conventional 2-D image presentation and, even though it may not be available in real-time as is 2-D fluoroscopy, tomosynthesis imaging, if performed at near real-time speeds, could be particularly helpful for guiding interventional procedures.

Thus, it can be seen that there is a need for a portable imaging apparatus that is capable of providing fluoroscopic imaging as well as depth imaging such as tomosynthesis imaging to help track progress for clinical and interventional procedures. There would be particular value in imaging apparatus and techniques that allow an imaging apparatus to switch rapidly between depth imaging and fluoroscopy at suitable angles, without requiring corresponding repositioning of the x-ray sources and detector.

SUMMARY

An object of the present disclosure is to address the need for imaging apparatus to support tracking of medical procedures internal to a patient. Tracking may be provided by 2-D fluoroscopic imaging in combination with tomosynthesis imaging for providing some measure of depth information. A related object of the present disclosure is to provide these different imaging functions from a single imaging apparatus that operates in different modes and easily switches between image acquisition modes, and display modes.

These objects are given only by way of illustrative example, and such objects may be exemplary of one or more embodiments of the invention. Other desirable objectives and advantages inherently achieved by the disclosed apparatus may occur or become apparent to those skilled in the art. The invention is defined by the appended claims.

In one embodiment, an x-ray assembly is configured to be energizable to emit ionizing radiation from one or multiple different spatial positions toward an imaging region of a patient. Control hardware energizes the x-ray assembly at predetermined times at one or more of the spatial positions. One mode of operation allows energizing the x-ray assembly one or more times from a first spatial position toward the imaging region of the patient, while a second mode of operation allows energizing the x-ray assembly multiple times each from a different one of the spatial positions. The control hardware is configured to switch an operating mode of the imaging system between the first and second modes during one medical image examination, or medical process occurring in the imaging region of the patient.

In another embodiment, a method of operating an imaging system includes providing a plurality of x-ray sources, energizing one of the x-ray sources multiple times at one predetermined position and capturing a first plurality of radiographic images of a subject thereby. The one or more x-ray sources are energized multiple times at different predetermined positions and a second plurality of radiographic images of the subject are captured thereby corresponding to the different predetermined positions. At least a portion of the captured images are used in reconstructing a tomosynthesis image. Furthermore, the step of capturing can be repeated while simultaneously reconstructing the tomosynthesis image. A collimator can be provided for each of the plurality of x-ray sources and adjusted accordingly.

In another embodiment, a method of operating an imaging system includes fixing a number of x-ray sources in preselected positions, energizing a one of the x-ray sources including fluoroscopy imaging a body tissue, and then terminating use of the first x-ray source and energizing a second x-ray source to continue imaging the body tissue. The x-ray sources can be positioned in a common plane, and/or in a single vacuum chamber, or in a curved two dimensional array.

This brief description of embodiments of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of embodiments of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3 is a diagram that shows an exemplary embodiment of a display/monitor mounted to a boom assembly of a mobile radiography unit according to the present disclosure.

FIG. 12B is a schematic diagram that shows how an acquired image may be used in two different modalities according to embodiments of the present disclosure.

DETAILED DESCRIPTION OF THE EMBODIMENTS

Figure 1:
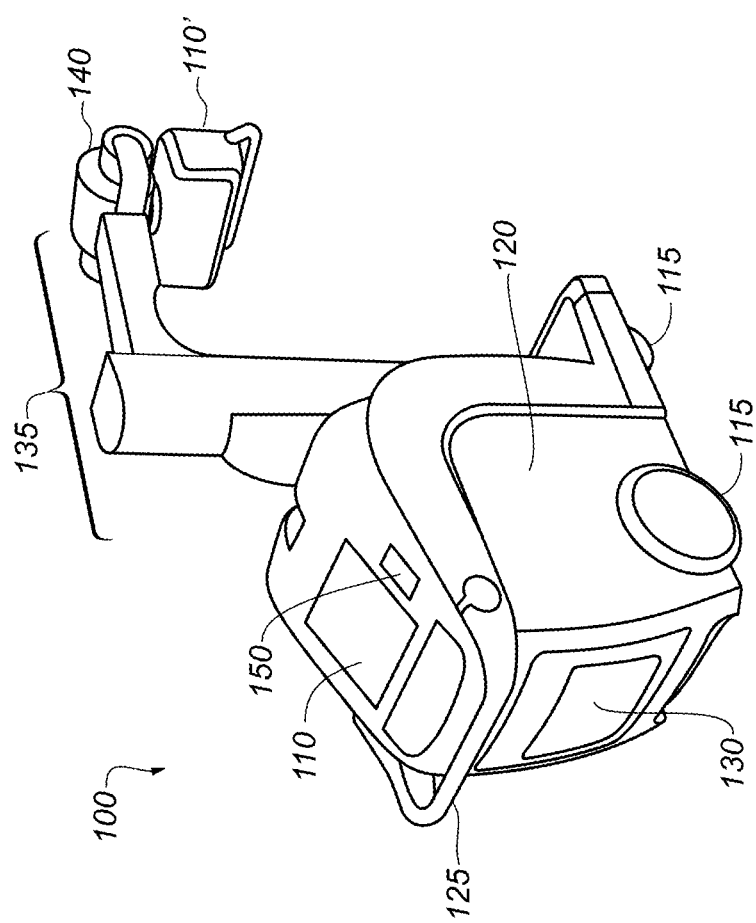
FIG. 1 is a diagram that shows a perspective view of an exemplary mobile radiography unit with two displays according to one embodiment of the present disclosure.

The following is a detailed description of the preferred embodiments, reference being made to the drawings in which the same reference numerals identify the same elements of structure in each of the several figures.

Where they are used herein, the terms "first", "second", and so on, do not necessarily denote any ordinal, sequential, or priority relation, but are simply used to more clearly distinguish one element or set of elements from another, unless specified otherwise.

In the context of the present disclosure, the terms "viewer", "viewing practitioner", and "observer", are considered to be equivalent and refer to the viewing practitioner or other person who views and manipulates an x-ray image on a display monitor or other viewing apparatus.

As used herein, the term "energizable" relates to a device or set of components that perform an indicated function upon receiving power and, optionally, upon receiving an enabling signal.

The term "actuable" has its conventional meaning, relating to a device or component that may be capable of effecting an action in response to a stimulus, such as in response to an electrical signal, for example.

The term "modality" is a term of art that refers to types of imaging. Modalities for an imaging system may be conventional x-ray radiography, fluoroscopy or pulsed radiography, tomosynthesis, tomography, ultrasound, MMR, or other types of imaging. The term "subject" refers to a patient that is being imaged, or a portion thereof, and, in optical terms, can be considered equivalent to the "object" of the corresponding imaging system. The patient may be human or animal, such as a mammal, and a region of interest may include a bodily region or a particular organ or tissue of the human or animal.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

In the context of the present disclosure, the term "depth image" refers to a reconstructed image that represents depth information obtained from processing multiple 2-D images or projection images of the subject, taken from different angles. Depth images may be obtained from tomosynthesis, which does not typically provide full 3-D representation, or from computed tomography (CT) that provides more complete depth information and is considered to provide 3-D imaging. The noun "projection" may be used to mean "projection image", referring to the 2-D image that may be captured and used with other projection images to reconstruct a depth image. Reference is made to U.S. Pat. No. 8,172,633 to Park et al., filed Apr. 4, 2007; U.S. Patent Application Publication No. 2011/0003109 by Slinker et al., filed Jul. 1, 2009; and U.S. Pat. No. 7,505,562 to Dinca et al., filed Apr. 19, 2007, all three of which are incorporated by reference herein in their entirety.

FIG. 1 is a diagram that shows a perspective view of a mobile radiography unit that may use one or more portable radiographic detectors or flat panel detectors adapted to acquire digital image data according to radiation received from the x-ray sources according to embodiments of the present disclosure. The exemplary mobile x-ray or radiographic apparatus of FIG. 1 may be employed for digital radiography (DR), pulsed radiography or fluoroscopy, and/or tomosynthesis. As shown in FIG. 1, a mobile radiography apparatus 100 may include a moveable transport frame 120 that includes a first display 110 and an optional second display 110' to display relevant information such as acquired radiographic images and related data. As shown in FIG. 1, the second display 110' may be pivotably mounted adjacent to the x-ray source 140 to be viewable/touchable in a 360 degree range.

The displays 110, 110' may be used to initiate or control (e.g., by way of touch screens) functions such as generating, storing, transmitting, modifying, and printing of an obtained image(s) and may include an integral or separate control panel (not shown) to assist in initiating functions such as generating, storing, transmitting, modifying, and printing of an obtained image(s). One or more of displays 110, 110' may be separable from the apparatus 100 frame. One or more of displays 110, 110' may act as display monitors for providing control messages and acknowledging instruction entry.

For mobility, the mobile radiographic apparatus 100 may have one or more wheels 115 and one or more handle grips 125 typically provided at waist-level, shoulder-level, or at other levels that may be used by an operator to guide the mobile radiographic apparatus 100 to its intended location. A self-contained battery pack (e.g., rechargeable) may provide source power, which may reduce or eliminate the need for operation near a power outlet. Further, the self-contained battery pack may also provide power to a motorized transport mechanism.

For storage, the mobile radiographic apparatus 100 may include an area/holder for holding/storing one or more digital radiographic (DR) detectors or computed radiography cassettes. The area/holder may be storage area 130 (e.g., disposed on the frame 120) configured to removably retain at least one digital radiography (DR) detector. The storage area 130 may be configured to hold a plurality of detectors and may also be configured to hold one size or multiple sizes of DR detectors and/or batteries therefor.

Mounted to frame 120 is a support member 135, a column that supports one or more x-ray sources 140, also called an x-ray tube, tube head, or generator that may be mounted to the support member 135. In the embodiment shown in FIG. 1, the supporting column (e.g., member 135) may include a second section, a type of boom that extends outward a fixed/variable distance from a first section where the second section may be configured to ride vertically up and down the first section to the desired height for obtaining the image. In addition, the support column may be rotatably attached to the moveable frame 120. In another embodiment, the tube head or x-ray source 140 may be rotatably coupled to the support member 135. In another exemplary embodiment, an articulated member of the support column that bends at a joint mechanism may allow movement of the x-ray source 140 over a range of vertical and horizontal positions. Height settings for the x-ray source 140 may range from low height for imaging feet and lower extremities to shoulder height and above for imaging the upper body portions of patients in various positions.

Figure 2:
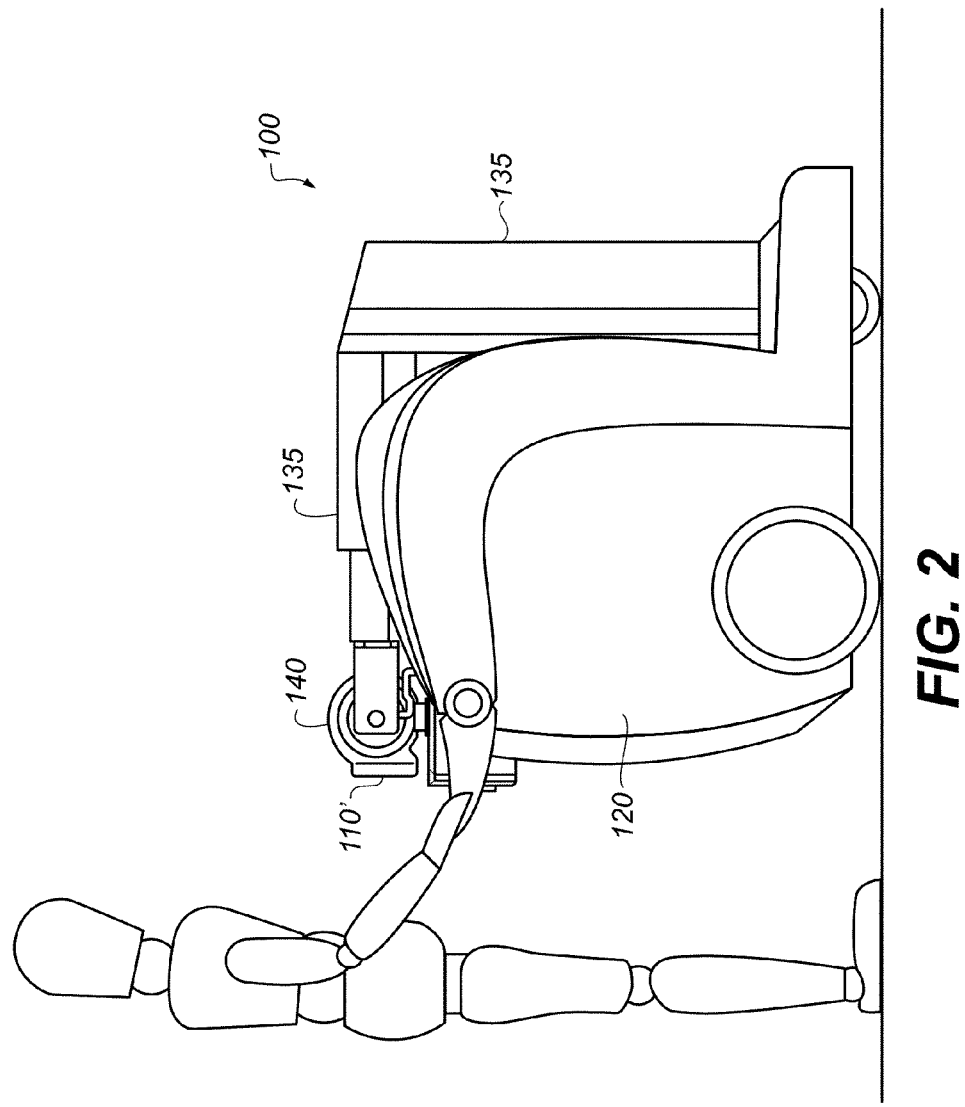
FIG. 2 is a diagram that shows a perspective view of an exemplary mobile radiography unit of FIG. 1 positioned for travel.

As shown in FIG. 2, for ease during transport of the mobile radiographic apparatus 100, the support member 135 and x-ray source 140 may be manipulated into a more compact arrangement whereby components are placed in closer proximity to frame 120. As shown in FIG. 2, the second display 110' may be configured so that it may be placed in a viewable position (e.g., operable) during transport of the mobile radiographic apparatus 100. When the mobile radiographic apparatus 100 is to be used for imaging, the support member 135 and x-ray source 140 may be extended from the frame 120 for proper positioning (e.g., by the operator, a user, or x-ray technician) and the second display 110' may be moved to another viewable position such as shown in FIG. 1.

FIG. 3 is a diagram that shows an exemplary embodiment of a display/monitor used as a second display 110' mounted to a boom assembly of a mobile radiography unit according to the present disclosure. As shown in FIG. 3, the second display 110' may be mounted to a collimator 345 of an x-ray source 340 of a support member 135 of a mobile radiography unit. In other embodiments, the collimator 345 may be rotatably mounted to the x-ray source 340 so that the collimator 345 (e.g., second display 110') may swivel at least about 90 degrees, at least about 180 degrees, or about 360 degrees. As shown in FIG. 3, the second display 110' may include a plurality of handles 341 coupled thereto for ease of positioning. Alternatively, the second display 110' may be mounted (e.g., rotatably) to an x-ray source 340 above a collimator 345 of the boom assembly of the mobile radiography unit.

The Applicants have recognized the need for an imaging apparatus that provides improved tracking of interventional and other medical procedures, wherein the tracking operation of the imaging system adapts to the needs of the practitioner and operates in both 2-D and depth imaging modalities. Moreover, the apparatus of the present disclosure shares acquired image data between imaging modalities, so that image data obtained for 2-D fluoroscopy may be reused for forming a tomosynthesis image that has depth data. Embodiments of the present disclosure also allow for updating the tomosynthesis image with partial information that has been obtained from fluoroscopic imaging, thus providing a wide range of imaging tools to the practitioner with reduced radiation dose to the patient. With improved visualization, interventional procedures may be performed in less time, further reducing radiation to patients and potentially using smaller concentrations of contrast agent. In addition, because embodiments of the present disclosure may utilize an array of smaller x-ray sources arranged in a geometric pattern, one embodiment may allow the imaging system to be adapted to the type of imaging and radiation angles necessary for acquiring useful images, or adapting different sequences of x-ray source energization to provide improved imaging from different angles without requiring re-positioning of the x-ray sources.

Figure 4A:
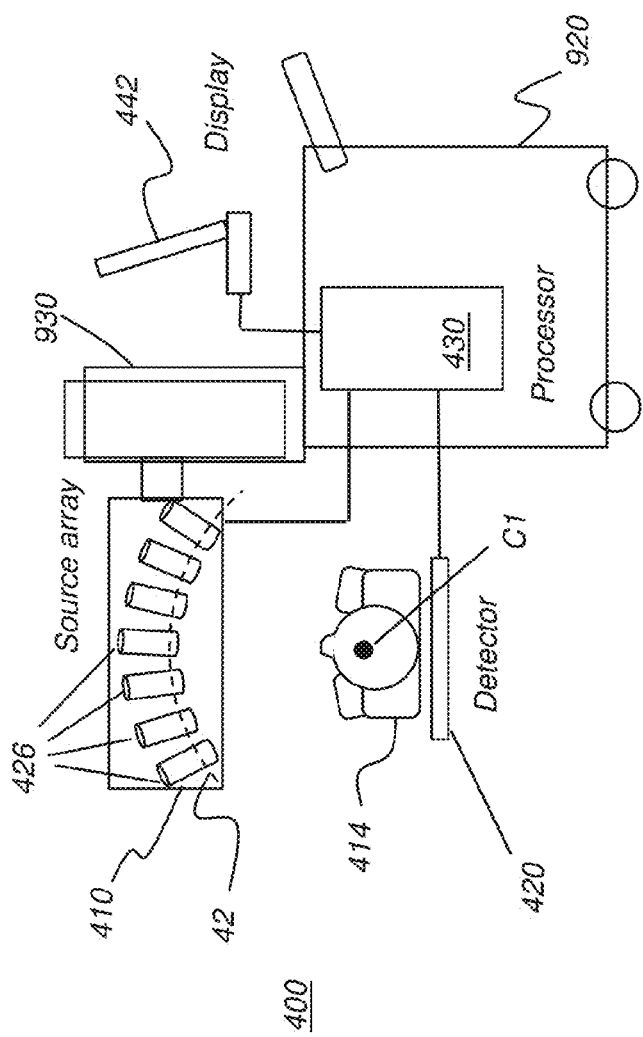
FIGS. 4A-4B are schematic diagrams that show a portable radiography apparatus according to embodiments of the present disclosure.

In one embodiment, as shown in schematic form in FIG. 4A, a portable or mobile hybrid fluoroscopy apparatus 400 for obtaining images of a patient 414 has an array 410 of x-ray sources 426 in a fixed geometric arrangement, each x-ray source 426 configured to be individually energized as part of a timed sequence of energizing a subset or all of the x-ray sources 426, and each x-ray source 426 in array 410 aimed to emit radiation toward a region of a subject, patient 414, to be imaged. In another embodiment, as shown in schematic form in FIG. 4B, a portable or mobile hybrid fluoroscopy apparatus 480 for obtaining images of a patient 414 has a source transport 411 for moving one or more x-ray sources 426 along a curved path 412 in the directions indicate by arrow 413 to position the one or more x-ray sources 426 at any of the same positions as the fixed sources 426 in the x-ray source array 410 or at positions in between those of the fixed x-ray source array 410. The single x-ray source 426 may be configured to be fired multiple times at one position such as in a fluoroscopy mode, or as part of a timed sequential firing at each of several positions, such as in a tomographic capture mode, as the x-ray source 426 is moved to firing positions along the curved path 412. The curved path 412 is configured to continuously aim the x-ray source 426 toward a region of the subject patient 414 as the x-ray source 426 is moved. Thus, the description that follows is equally applicable to embodiments of the mobile hybrid fluoroscopy apparatuses 400 and 480.

An x-ray detector 420 may be separable from a support column 930 and may be adapted to capture the digital x-ray images. X-ray sources 426 may be disposed in a single plane, multiple planes, a two-dimensional curved or planar array, or combination thereof in the embodiment of the mobile hybrid fluoroscopy apparatuses 400, and the source transport 411 of the mobile hybrid fluoroscopy apparatuses 480 may be configured to move the single x-ray source 426 in a single plane, multiple planes, a two-dimensional curved or planar array, or combination thereof. X-ray sources 426 of the mobile hybrid fluoroscopy apparatuses 400 may be disposed in a single vacuum chamber or may be configured so that multiple sources share a common vacuum chamber or so that each source has its own vacuum chamber. X-ray detector 420 may be de-coupled from array 410 or transport 411, e.g., a free-standing detector, and be manually repositionable so that a variable distance between array 410 or transport 411 and detector 420 may be provided.

An image processor 430, such as a computer server or workstation, processes the acquired digital images and generates either 2-D fluoroscopy or depth images as needed during a medical procedure. A processing system having control logic processor 430 loads and executes a sequence of instructions, stored as a control program, for obtaining a stored imaging pattern by energizing a subset or all of the x-ray sources in a programmed sequence, wherein the programmed sequence controls which of the x-ray sources are included in the subset and controls timing for energizing each of the x-ray sources. According to an alternate embodiment of the present disclosure, processor 430 may be a dedicated Graphical Processing Unit (GPU). The GPU may be used as a graphic display processor with a fixed pipeline to a more capable processor for general purpose computing, matrix computing, image processing, simulation and medical imaging using parallel processing over the programming pipeline. As one example, GPU architecture and its parallel processing capabilities have been utilized for providing hardware-accelerated volume image rendering and other imaging, as described in U.S. Patent Application No. 2006/0227131 entitled "Flat Texture Volume Rendering" by Schiwietz et al., which is incorporated by reference herein in its entirety.

A display 442 may be in signal communication with processor 430 and may be adapted to display the acquired images. A mobile transport frame 920 has column 930 that serves as a support structure for extending array 410 or transport 411 toward patient 414 or other subject to be imaged. X-ray source array 410 or transport 411 may remain stationary during imaging. Alternatively, x-ray source array 410 or transport 411 may be moved during imaging, independent of the stationary detector 420. The array of x-ray sources 410 in FIG. 4A may have three or more x-ray sources 426 and may be geometrically arcuate in a plane perpendicular to the image plane in the embodiment that is shown, but may have any of a number of alternate geometric configurations. Considered geometrically, the arc center of the source array 410 or the transport 411, shown as C1 in FIGS. 4A and 4B may be generally located within the patient being imaged, by placing the patient at the arc center, or within about one meter of the patient. An arc 42 is represented as a dashed line in FIG. 4A and the curved path 412 of FIG. 4B may be configured to be parallel thereto.

Figure 4B:
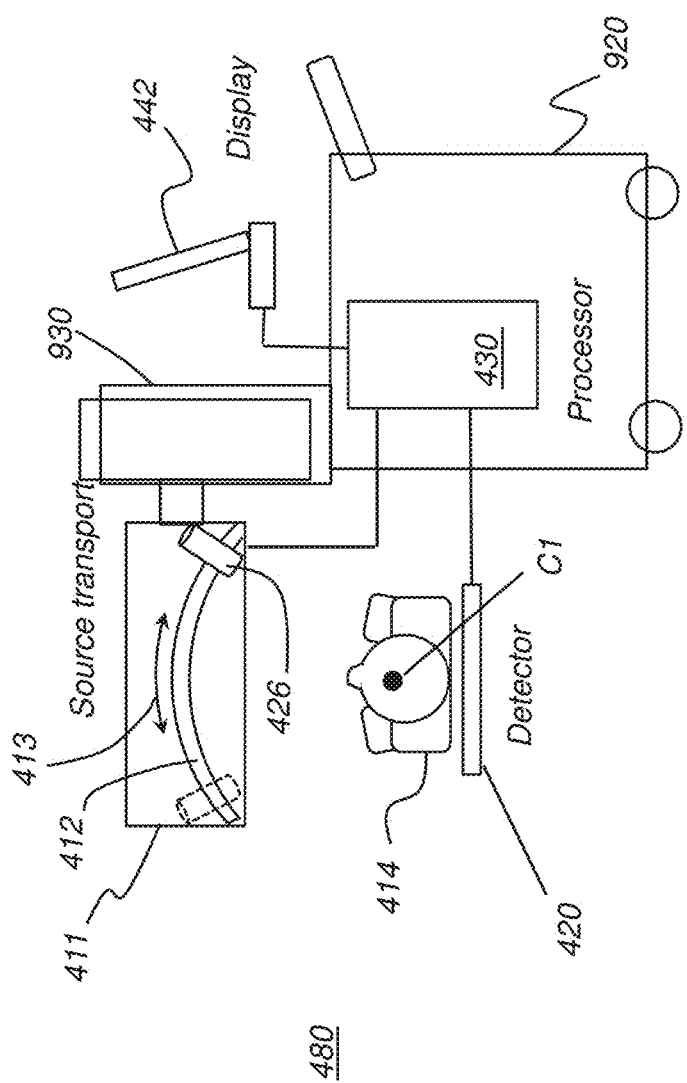

The source array 410 could alternately be designed so that fixed sources 426 are peripherally arranged to be geometrically arcuate in a plane parallel to the image plane, or may have some other overall shape. Detector 420 may be positionable independent of source array 410 and transport 411. According to an embodiment of the present disclosure, as shown in FIGS. 4A and 4B, transport frame 920 also houses processor 430 for 2-D and depth image processing and presentation.

Figure 5:
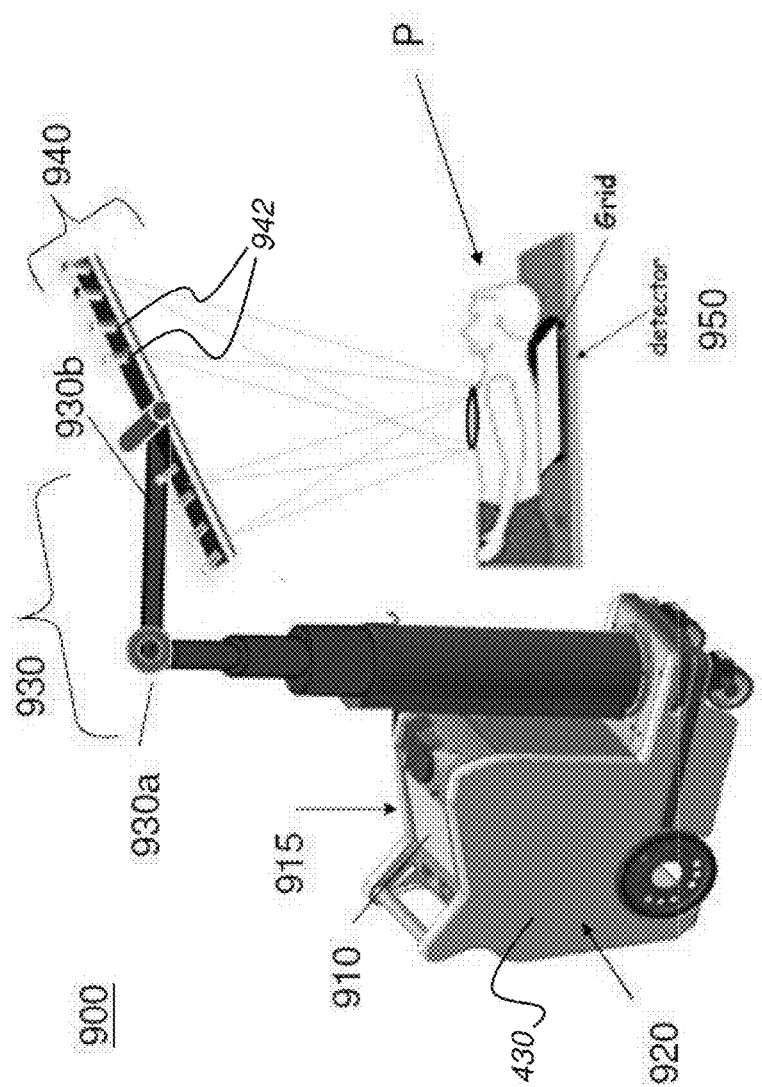
FIG. 5 is a diagram that shows a perspective view of a mobile radiography unit that may provide fluoroscopic and tomosynthesis imaging according to embodiments of the present disclosure.

FIG. 5 is a diagram that shows a perspective view of a mobile radiography apparatus 900 that may provide both fluoroscopic or pulsed radiography and tomosynthesis imaging capability according to embodiments of the present disclosure. According to an embodiment of the present disclosure, a mobile radiography apparatus 900 may operate as a tomosynthesis or fluoroscopy system, or a system adapted for other volume imaging modes. As shown in FIG. 5, the mobile radiography apparatus 900 may include a movable transport frame 920. Mounted to the moveable transport frame 920 may be a support column 930 that supports an x-ray source array 940. As shown in FIG. 5, support column 930 may include a second section 930b that extends as a boom outward a fixed/variable distance from a first section 930a, where the second section 930b may be configured to move (e.g., ride vertically) up and down the first section 930a to the desired height for obtaining the projection images. The system also includes a digital x-ray detector 950 that may be in signal communication with a system controller 915. Signal communication may be provided either wirelessly or in wired or tethered form, so that detector 950 may be connected to system controller 915 contained inside the moveable transport frame 920. Detector 950 may be separately positionable, independent of x-ray source array 940 components. The system controller 915 may implement and/or control the functions of the mobile radiographic/tomosynthesis system 900 (e.g., functions provided through a console or control displays 110, 110' in FIG. 1). The system controller 915 may include a general purpose processor, digital computer, microprocessor, RISC processor, signal processor, CPU, GPU, arithmetic logic unit (ALU), video digital signal processor (VDSP), dedicated processor, and/or similar computational machines, programmed for a range of positioning and imaging functions according to the teachings of the present disclosure, as will be apparent to those skilled in the radiography imaging arts.

In certain exemplary embodiments, mobile radiography apparatus 900 may provide a tomosynthesis capability. A moveable mounted x-ray source array 940 may, in addition, be supplied with a plurality of multiple individually controlled x-ray sources 942, such as more than three sources 942, to provide a distributed x-ray source array with a variable excitation pattern. FIG. 5 shows an embodiment of mobile radiography apparatus 900 where multiple individually controlled x-ray sources 942 in a linear arrangement or pattern provide distributed x-ray sources in an array. As shown in FIG. 5, x-ray source array 940 may alternatively include a plurality of distributed x-ray power sources 942 where at least one central source of the distributed x-ray power sources has full (e.g., standard) x-ray power. The central source, for example, may have a wide range of kVp settings, such as from about 50 kVp to about 150 kVp, and high maximum mA output, such as from about 10 mA to about 400 mA, in order to accommodate many different exam types for general radiography.

The distributed sources that form the array may be disposed in a prescribed spatial relationship. The distributed sources may include lower power x-ray sources, which may also mean a narrow range of kVp settings, such as from about 60 kVp to about 120 kVp for example, or such as from about 30 kVp to about 130 kVp, and a lower maximum mA output, such as from about 1 mA to about 100 mA. X-ray source array 940 may use one or more collimators that adjust to form beams that are directed towards the detector 950 and/or a patient P. The x-ray source array 940 may also include positioning mechanisms, such as motors, that allow for moving one or more sources or collimators and directing the beam more accurately towards the detector 950 and/or patient P. The moveable transport frame 920 may include first display 910, which may be part of a control console to control at least the x-ray source array 940. Further, the system controller 915 may coordinate operations of the x-ray source array 940, detector 950, and moveable transport frame 920 (e.g., via operator actions using the first display 910). The system controller 915 may control operations of the x-ray source array, which may include collimator settings, positioning devices and triggering of image acquisition by emission of x-rays from the sources. For example, the system controller 915 may control x-ray emission for tomosynthesis, or fluoroscopy imaging procedures and/or for general radiography imaging procedures. The system controller 915 also may control operations of detector 950, which may include triggering of image acquisition process and transmission of the acquired images back to the controller. In addition, the system controller 915 may control the movement of the transport frame 920.

Array of X-Ray Sources

The x-ray sources may be, for example, a distributed array of field-emission based x-ray sources, such as sources having carbon nanotube (CNT) cathodes, which may be peripherally arranged about a central thermionic source. The x-ray sources may be stationary or relatively fixed in position with respect to each other within the array; the array itself may move as a single unit. This type of x-ray source may be capable of rapid on/off switching on the order of microseconds. Other suitable x-ray sources may include paired pulsed conventional fluoro-capable thermionic sources that are spatially separated. These options provide sufficient x-ray fluence with short exposure times and simultaneously allow exposure sequences without overheating. A carbon nanotube x-ray source may include one or more cathodes within a vacuum chamber, wherein each cathode may be formed from a large number of individual carbon nanotubes that are subject to excitation energy and thereby emit electrons that are accelerated toward one or more anodes in the chamber.

Figure 6:
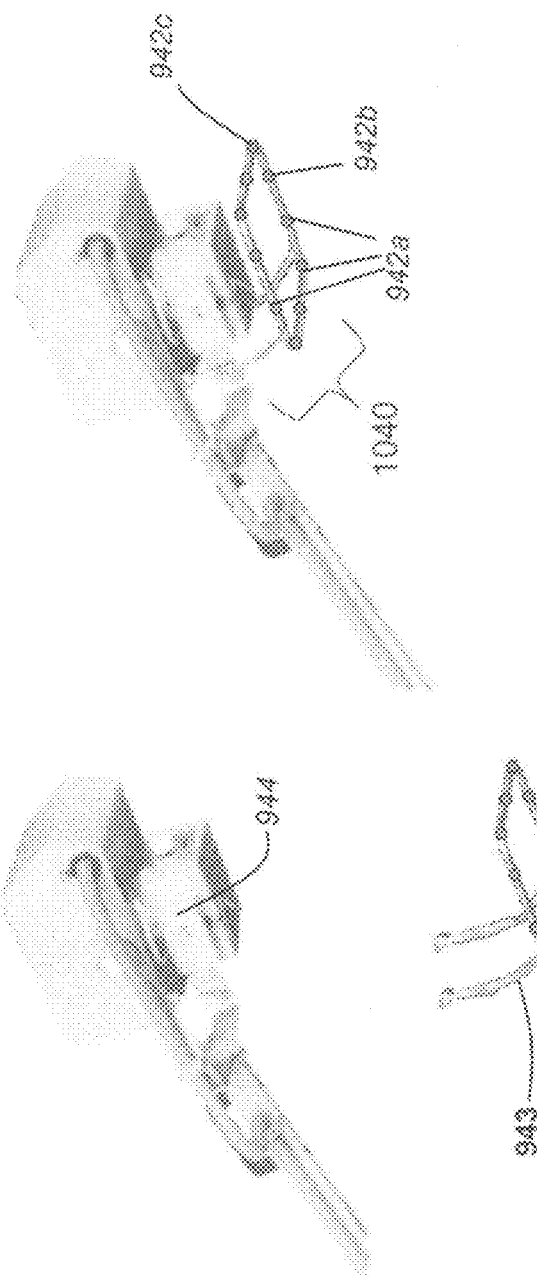
FIG. 6 is a diagram that shows x-ray source assemblies for exemplary mobile radiographic imaging systems including an x-ray source array embodiment that may include first and second radiographic x-ray sources and additional x-ray sources according to the present disclosure.

The diagram of FIG. 6 shows an x-ray source array 1040 of a mobile radiographic imaging system that includes a first radiographic x-ray source 944 of thermionic type and collimator, and a second, third, and additional x-ray sources 942a, 942b, 942c, and so on, that may be individually adjusted (e.g., collimated) and either permanently attached or attached when needed (e.g., detachable). As shown in FIG. 6, according to an embodiment of the present disclosure, the first radiographic x-ray source 944 may be a central one of the distributed sources. Alternatively, the first radiographic x-ray source may be thermionic, positioned at a center of the second array of peripherally distributed sources. As shown in FIG. 6, the first radiographic x-ray source 944 may be a mobile/portable x-ray source/tube and may be a different type of x-ray source from the second distributed array of lower power carbon-nanotube x-ray sources. Other types of standard radiography and distributed array sources may be used. Detachable sources or the full detachable array 410 may be separately mounted from the support structure of fluoroscopy apparatus 400 (FIG. 4A) or supported at one or more positions around the patient.

Figure 7:
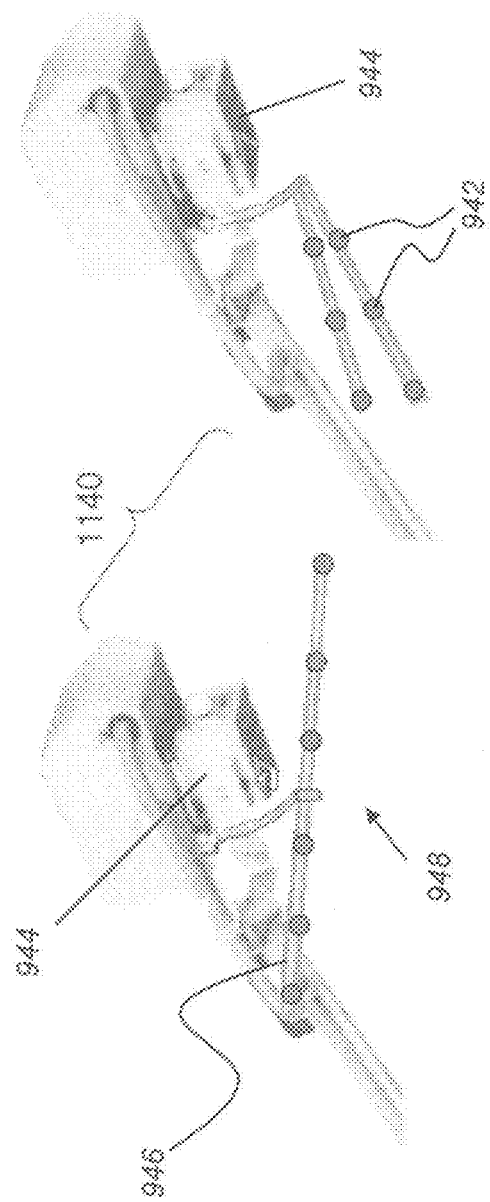
FIG. 7 is a diagram that shows alternate x-ray source assemblies for exemplary mobile radiographic imaging systems including an x-ray source array embodiment that may include first and second radiographic x-ray sources and additional x-ray sources according to the present disclosure.
Figure 8A:
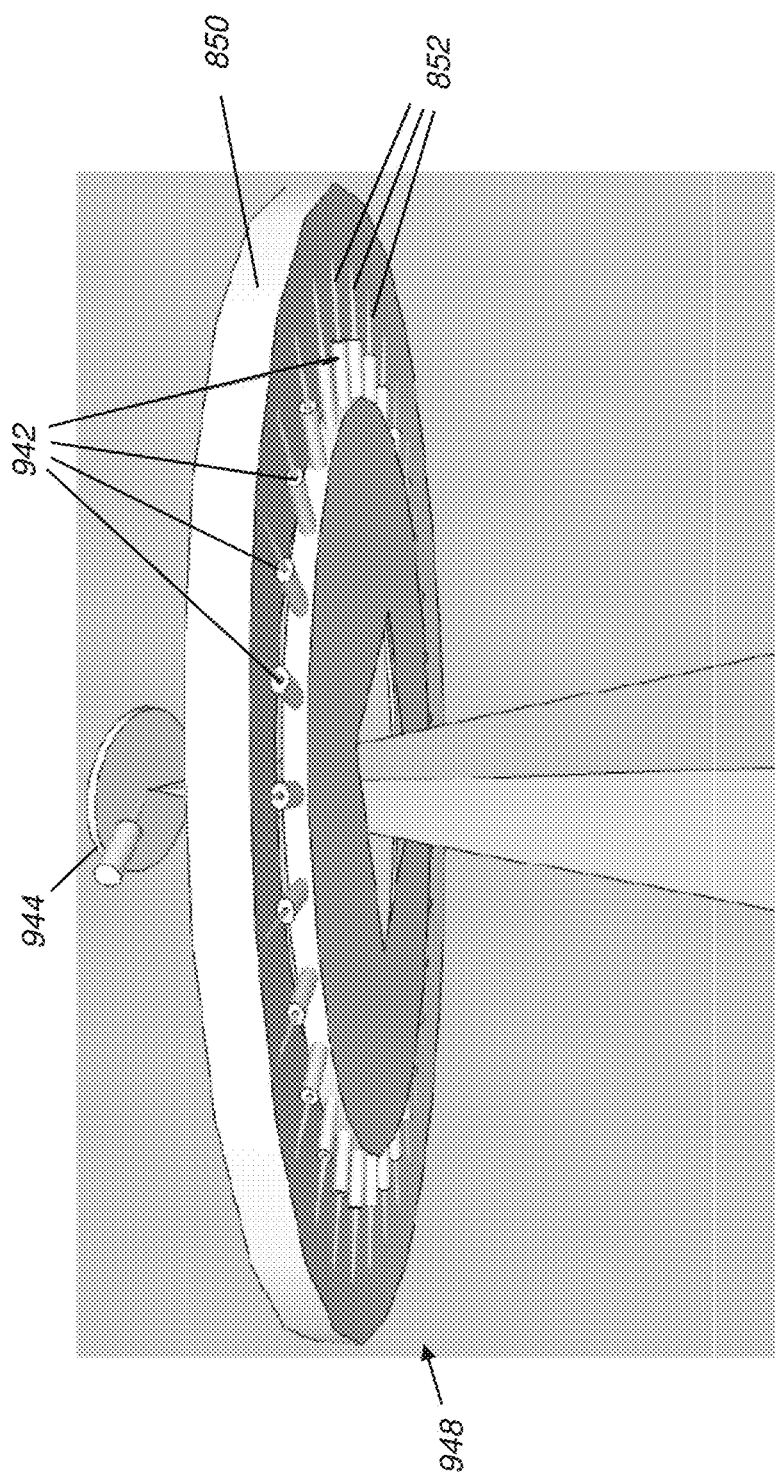
FIG. 8A is a perspective view showing an arrangement of radiation sources for imaging according to an embodiment of the present disclosure.
Figure 8B:
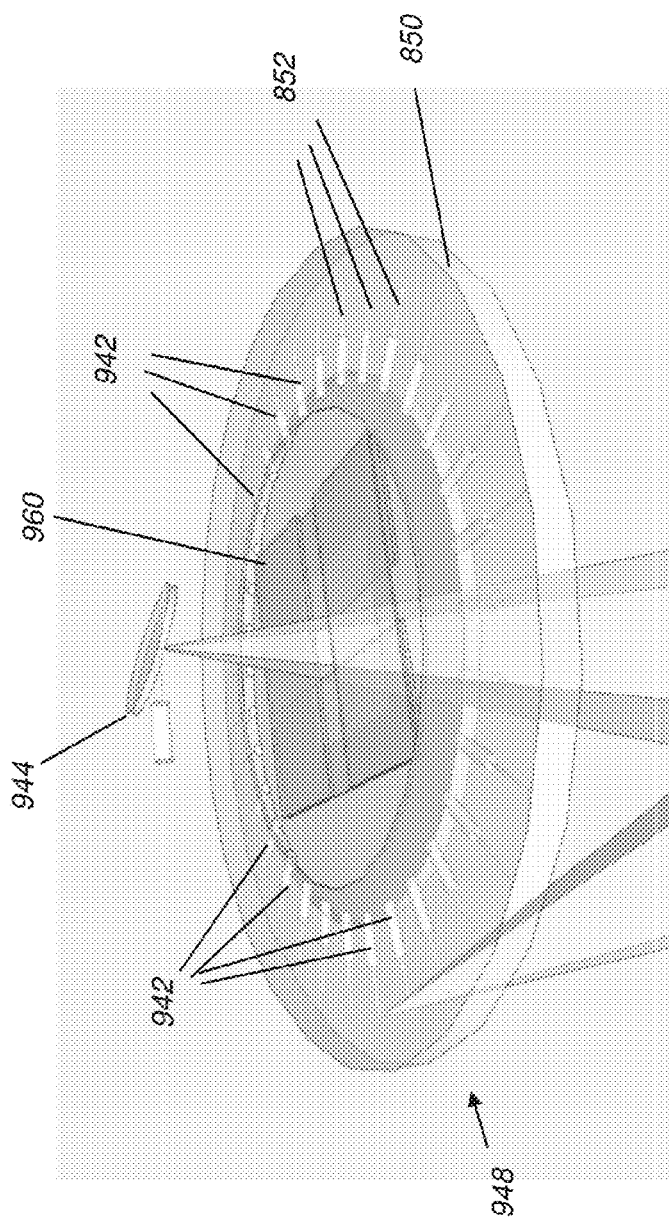
FIG. 8B is a perspective view from above showing an arrangement of radiation sources for imaging according to an embodiment of the present disclosure.
Figure 8C:
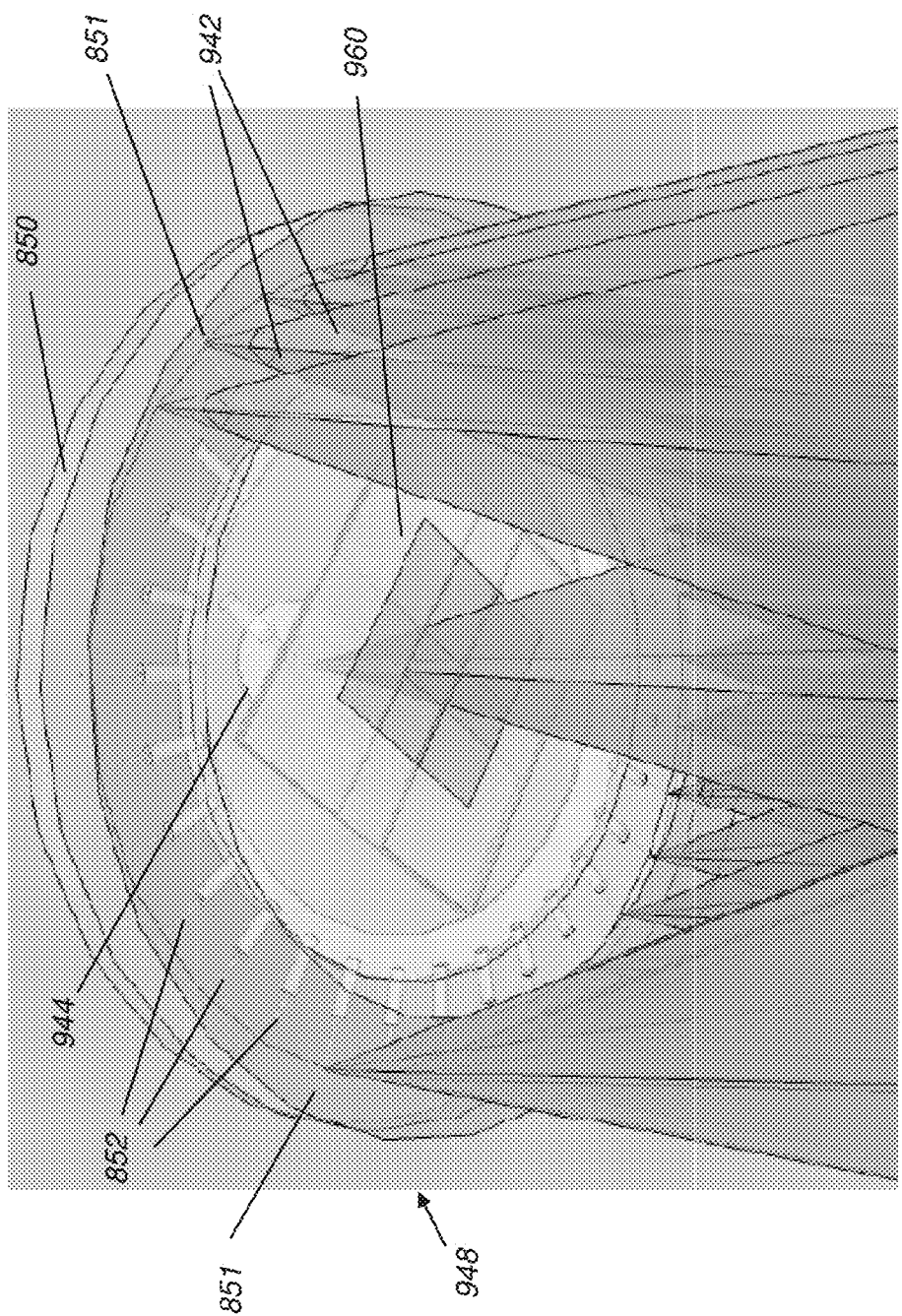
FIG. 8C is a perspective view from below showing the arrangement of radiation sources shown in FIGS. 8A and 8B for imaging according to an embodiment of the present disclosure.
Figure 8D:
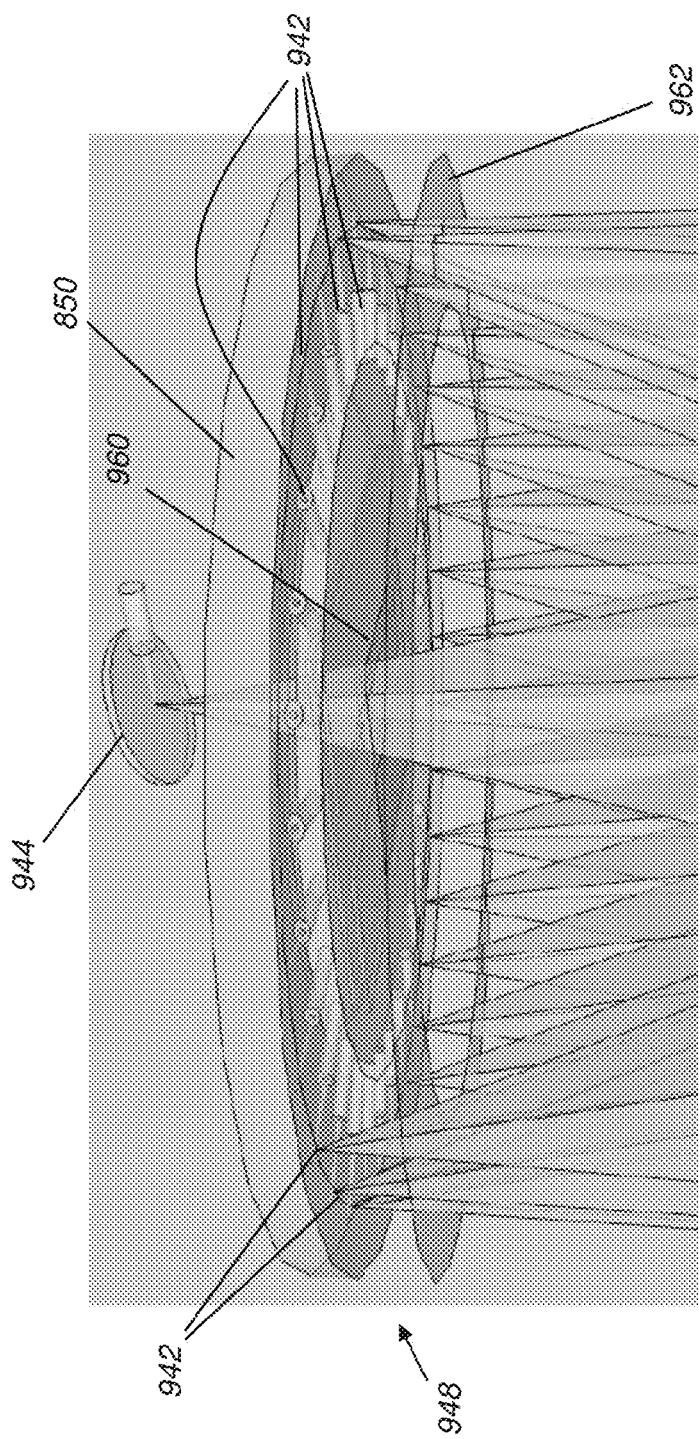
FIG. 8D is a perspective view showing an arrangement of radiation sources for imaging along with collimators for the source array according to an embodiment of the present disclosure.

The diagram of FIG. 7 shows an alternate embodiment of an x-ray source array 1140 of a mobile radiographic imaging system. The linear x-ray source array 1140 may include a directed first radiographic x-ray source 944 and a directed second x-ray source array 948 comprising a distributed source attachment (e.g., linear) that may be either permanently attached or attached when needed, e.g. as a detachable fixture 943 fixing sources 942a-c. As shown in FIG. 7, the first radiographic x-ray source may be positioned at a center of the array of distributed sources. In one embodiment, the first radiographic x-ray source may be a central member of the array 948 of distributed sources. In one embodiment, the plurality of distributed x-ray sources 942 may be mounted along a support 946. In one embodiment, the plurality of distributed x-ray sources 942 may have a prescribed spatial geometric relationship, where the prescribed spatial geometric relationship may be one or more linear tracks, 2-D tracks, curves, polygons, rectangles or 3D paths. In one embodiment, collimated distributed sources may be on a curved support to maintain a single distance from a corresponding point on a detector. Exemplary distributed source attachment may have a first position for use and a second position for storage (e.g., folded as shown in FIG. 7) when not used.

FIGS. 8A, 8B, 8C, and 8D show various embodiments of source array 948 with sources 942 in a generally elliptical or circular geometric arrangement with source 944 centered within the circle. According to an embodiment of the present disclosure, there may be about 64 sources 942 in a circular arrangement of about 32 cm diameter; the diameter may be varied as well as the curvature of the array or angular disposition of the sources within the array. An elliptical, polygonal, or randomized source arrangement may alternately be used to form a closed geometric loop of sources. A circle is one form of ellipse or, even more generally, a closed loop or closed curve structure. Triangles, squares, rectangles, pentagons, and hexagons are forms of polygons. Sources may also be distributed in a geometrically irregular arrangement.

In the FIG. 8A-8D arrangement, a collimator 960 may be provided for source 944. Additional collimators 962 provide collimation for individual sources 942. According to an embodiment of the present disclosure, each individual source 942 has its own collimator 962, as in the embodiment shown in FIG. 8D, for example. Each collimator may be adjustable to accommodate the angle between the x-ray source and detector. A number of subsequent figures intentionally omit showing the collimator 962 in order to show other details more clearly.

Figures 9A, 9B:
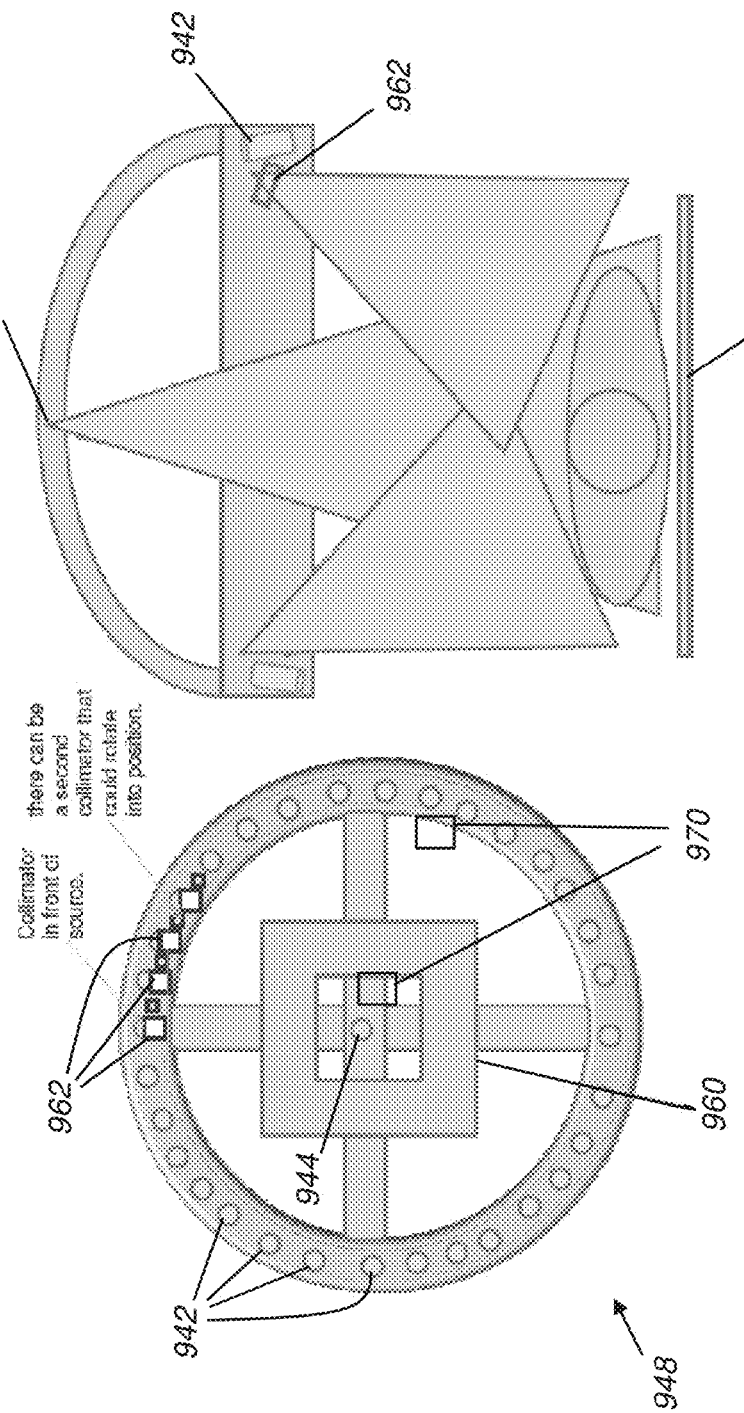
FIG. 9A is a bottom view showing the array of x-ray sources.
FIG. 9B is a side view showing exemplary emitted beam patterns from the array of x-ray sources of FIG. 9A.
Figure 10:
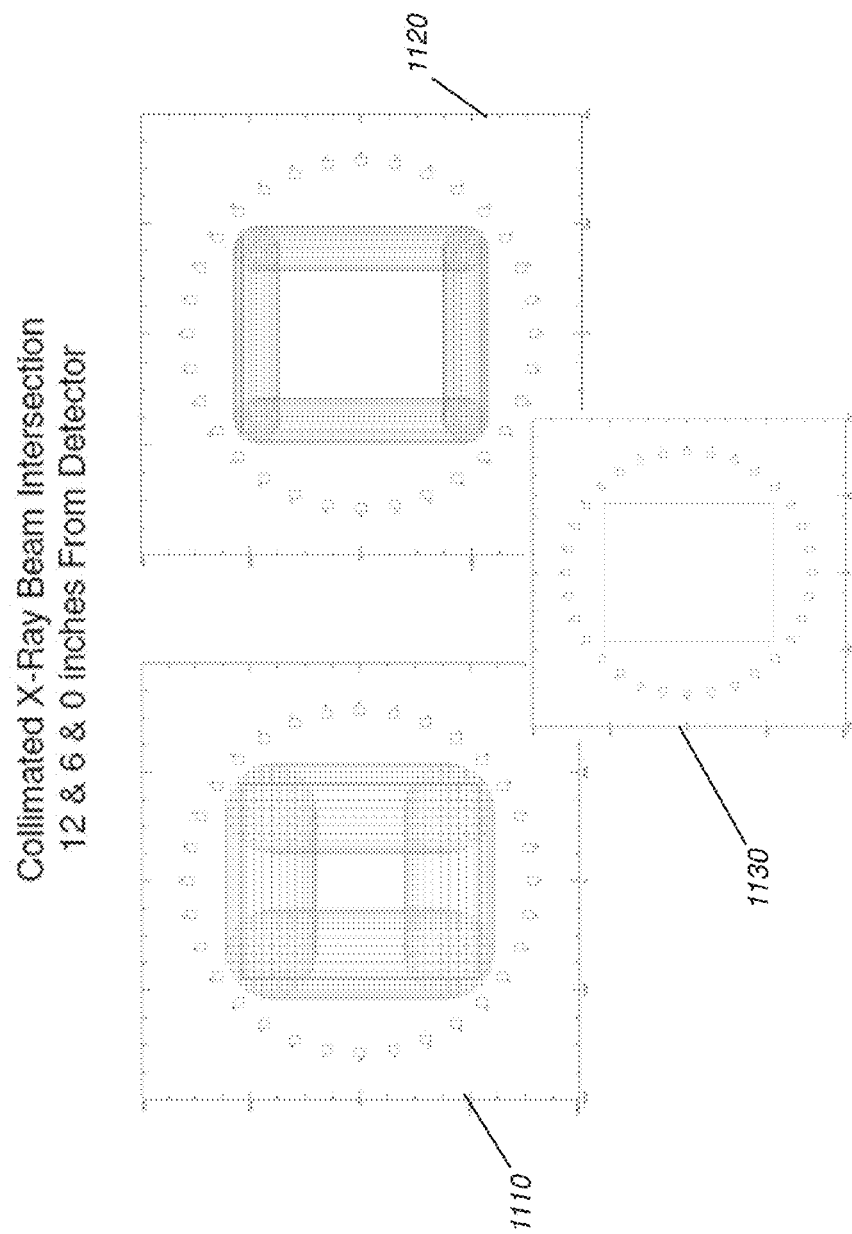
FIG. 10 is a schematic view that shows the collimated beam intersection patterns at different distances from the source.

FIG. 9A shows, from a bottom view, an exemplary configuration of radiation sources 942 for radiography and tomosynthesis imaging similar to those shown in FIGS. 8A-8D. FIG. 9B shows a side view. The schematic view of FIG. 10 shows the intersection of collimated x-ray beams with planes at different distances from the detector 950. In 1110, the beam intersects a plane at about 12 inches from the detector. In 1120, the beam intersects a plane at about 6 inches from the detector. In 1130, the beam intersects a plane proximate to or at the detector.

The x-ray source array 948 may be part of a portable radiography system, as shown and described as mobile radiography apparatus 900 with reference to FIGS. 1, 2, 4, and 5, or may be installed in a fixed position. With either a portable or fixed x-ray source configuration, the source array 948 may be used with a detector 950 that may be portable and not physically coupled to source array 948.

Figure 11:
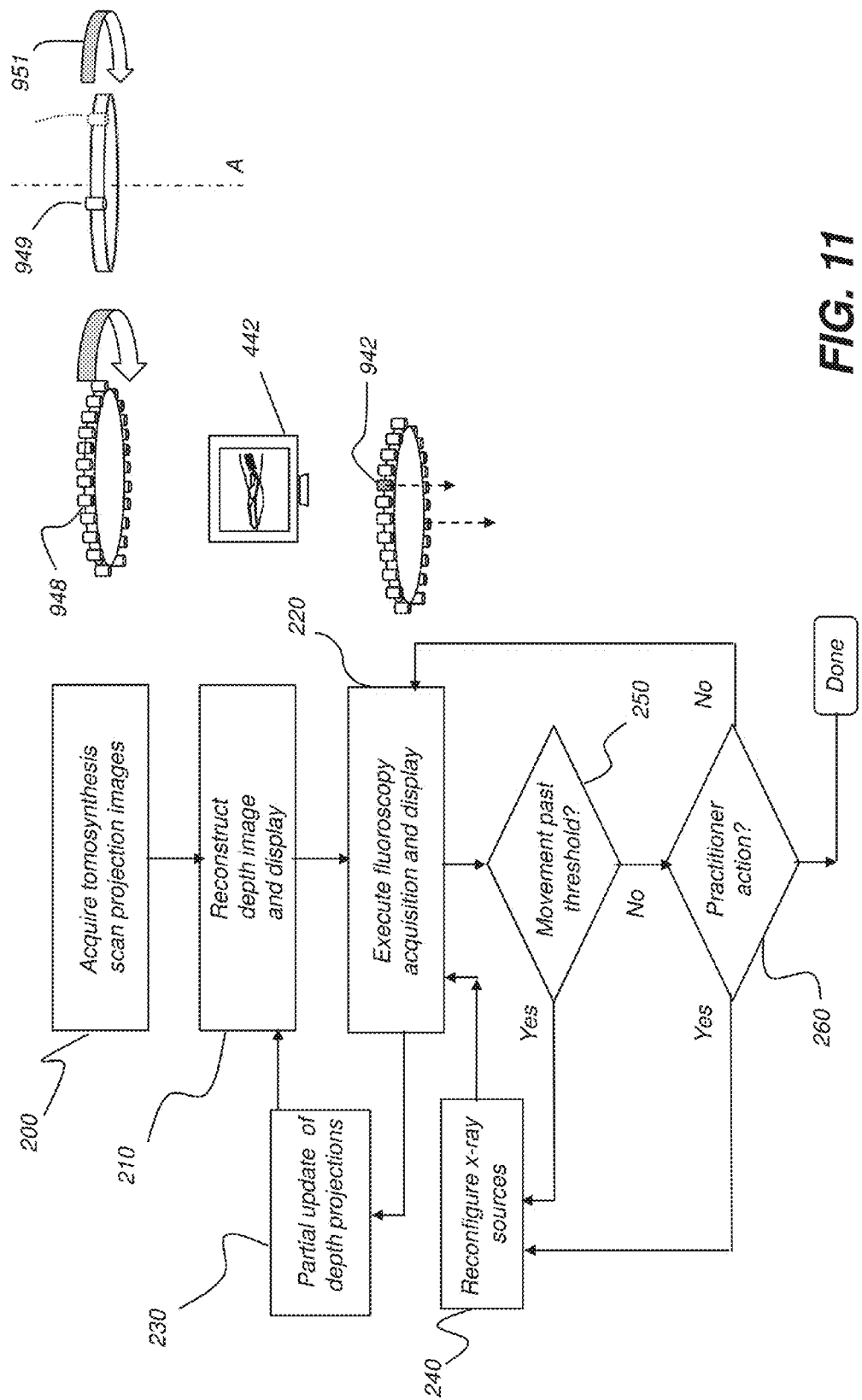
FIG. 11 is a logic flow diagram that shows a processing sequence for hybrid operation in tomosynthesis and fluoroscopy modes according to embodiments of the present disclosure.

The logic flow diagram of FIG. 11 shows an exemplary programmed sequence of operation for an imaging apparatus that uses x-ray source array 948, or one or more movable x-ray sources 949 for combined fluoroscopic and tomosynthesis imaging. The movable one or more sources 949 may be configured to be revolved about central axis A as indicated by the arrow 951 to the same positions as each of the fixed sources in source array 948, as shown in FIG. 11, and to positions between those of the fixed sources of source array 948. The programmed sequence thus allows successive imaging for two or more modalities such as conventional projection radiography, fluoroscopy or pulsed radiography, and tomosynthesis, using the same fixed geometric arrangement 948 or the movable configuration 949. This advantageously provides the different types of images within the same spatial configuration. According to the stored, programmed imaging sequence, an initial scanning step 200 may obtain the projection 2-D images that are used for reconstruction of the depth image in tomosynthesis processing. Scanning step 200 may use multiple sources in array 948 and may use each of the x-ray sources in the array 948, acquiring an image with the energization of each source. Scanning step 200 may also use the one or more movable sources 949, acquiring an image at each programmed position of the source 949 as it is revolved into positions about axis A. In a reconstruction and display step 210, image processor 430 uses the scanning step 200 results and generates, using a reconstruction algorithm, the depth image for presentation on display 442. A fluoroscopy step 220 may be executed, in which one or more individual sources 942 in array 948, or the one or more sources 949, are energized in order to generate 2-D fluoroscopic images. Significantly, the array of sources 948 remain in their fixed positions when the imaging modality is changed, such as when changing from tomosynthesis to fluoroscopy or from fluoroscopy to tomosynthesis. With regard to the movable one or more sources 949, it may remain in a fixed position when the imaging modality is changed or it may begin or stop motion (revolving) when the imaging modality is changed, such as when changing from tomosynthesis to fluoroscopy or from fluoroscopy to tomosynthesis. During step 220, an update step 230 executes, in which the depth image that was generated in reconstruction and display step 210 may be at least partially updated according to the acquired fluoroscopy image content that corresponds to some of the image projections originally obtained for the depth image. An optional auto-reconfiguration step 240 may be executed based on detected movement of a catheter or other device or substance past a threshold position, or based on operator movement or action, such as an explicit instruction, signal, button activation, or on detection of a change in the focus of operator attention, according to decision steps 250 or 260. Reconfiguration step 240 may change the excitation pattern of the x-ray source or sources used for the fluoroscopic imaging sequence and may continue the sequence, obtaining further fluoroscopic data.

In addition to adapting its fluoroscopic imaging behavior based on motion information or practitioner prompting, the process of FIG. 11 allows periodic update of the depth image that originates from tomosynthesis reconstruction according to at least some portion of the image content that may be subsequently obtained from fluoroscopic imaging. When the same x-ray source is used for tomosynthesis and fluoroscopy imaging, update of the tomosynthesis image may be performed based on subsequent fluoroscopic content. As the angular aspect of the fluoroscopic image changes, another portion of the projection images that were used to reconstruct the depth image may be updated; thus, the corresponding tomosynthesis projection may be refreshed accordingly. Thus, change in image capture angle may cause a corresponding change in the image data content used for reconstructing the tomosynthesis image.

Figure 12A:
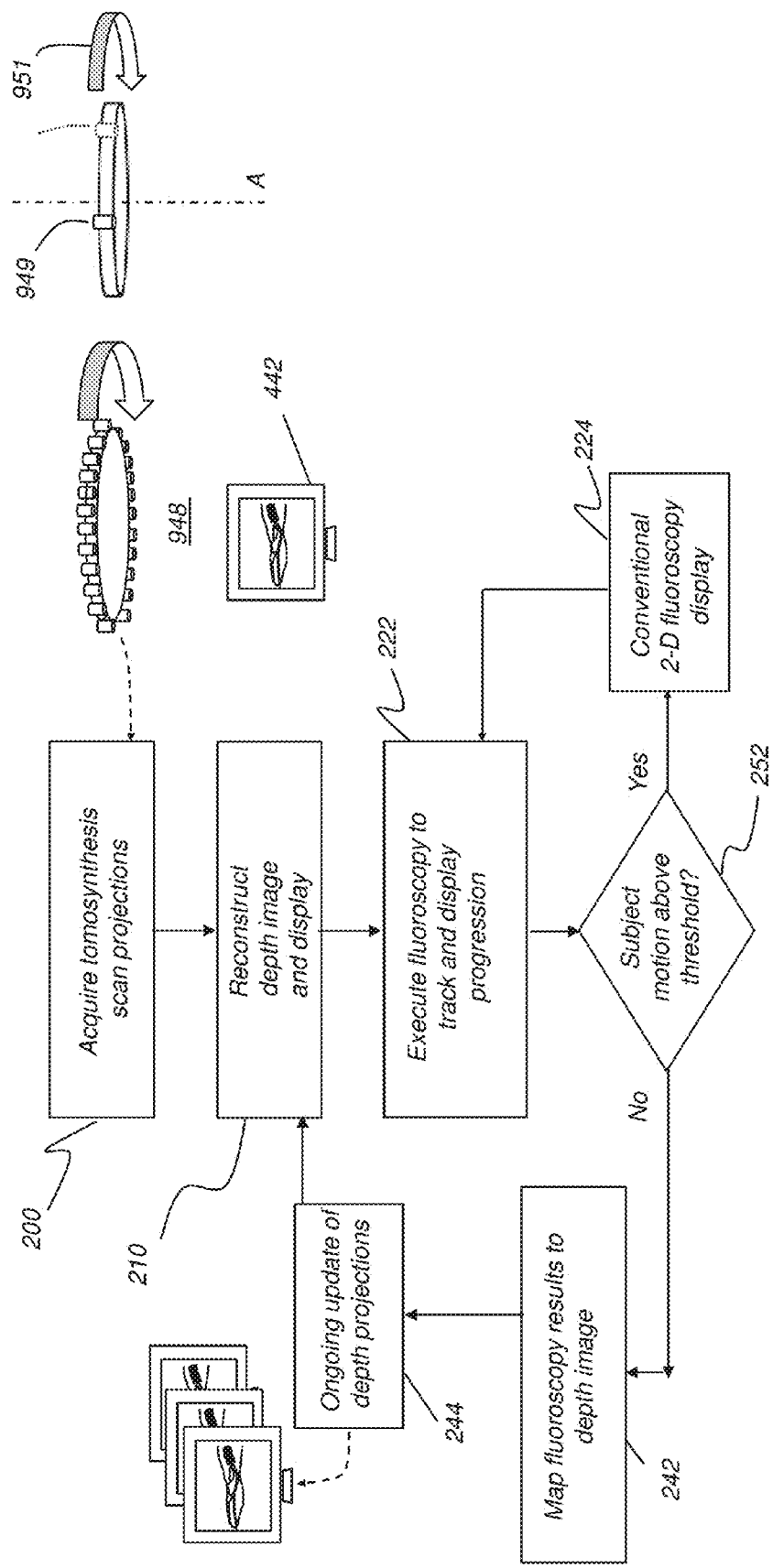
FIG. 12A is a logic flow diagram that shows a processing sequence for using depth imaging fluoroscopy according to embodiments of the present disclosure.

The logic flow diagram of FIG. 12A shows an alternate sequence of operation for providing a hybrid fluoroscopic depth imaging that dynamically adjusts operation based on how quickly the system is able to respond to detected motion of the subject. Where detected motion is relatively slow during a procedure, fluoroscopic image capture may not be used to refresh a 2-D display, but rather used to provide an updated depth imaging display. Where motion or movement speed is above a predetermined threshold, the depth image may either not be updated, or may be updated periodically, but the 2-D fluoroscopy display may be continuously updated. Scanning step 200 and reconstruction and display step 210 form the depth image from tomosynthesis imaging. Each projection image obtained in the tomosynthesis scan has corresponding angular sequence information, allowing frame-by-frame update of tomo synthesis projections with fluoroscopic content as fluoroscopy proceeds. A fluoroscopy step 222 then executes a fluoroscopy or pulsed radiography imaging sequence, obtaining a succession of 2-D fluoroscopic images for display. A decision step 252 checks for movement of the subject content to determine whether to continue with conventional 2-D fluoroscopy in a fluoroscopy step 224 or to update the depth image from tomosynthesis using the fluoroscopic image data that was obtained. Where movement is slow, a mapping step 242 maps fluoroscopy imaging results to the depth image projections to provide information for an update step 244. Update step 244 provides the newly obtained fluoroscopy image data to reconstruction and display step 210 so that the depth image can be reconstructed.

In one method of operation, a fluoroscopy sequence may be performed utilizing some or all of the sources 948 in a pulsed sequence, and displayed on display 442. Such an imaging sequence may not significantly affect observable phenomena displayed on display 442 as viewed by an operator of the imaging system as compared with the conventional fluoroscopy mode of using only one pulsed source. The set of fluoroscopy images obtained this way may be captured and stored in order to be used to generate a depth image using tomographic reconstruction methods as described herein.

For the sequence of FIG. 12A, movement may be detected by image analysis of the fluoroscopic image data stream, using methods well known in the imaging arts for detecting subject movement from successive images. By tracking movement in this sequence, the system adapts to provide different types of image display for the practitioner, with the added benefit of depth display when there is sufficient time for update of the reconstructed image. According to an embodiment of the present disclosure, viewer override is also provided, so that movement detection does not determine how imaging results are provided; instead, the practitioner decides to maintain either depth imaging or fluoroscopy imaging during parts of a procedure.

FIG. 12B shows how acquired projection images 952 may be used in two different modalities according to an embodiment of the present disclosure. Although FIG. 12B illustrates a fixed source array configuration 948, as described above with reference to FIGS. 11 and 12A, an embodiment using the one more movable source(s) 949, as described above with reference to FIGS. 11 and 12A, may be used and is equally applicable. Thus, the following description referring to sequential firing of fixed sources in source array 948 may also be implemented using the one or more movable source(s) 949 being moved (revolved) into equivalent positions for firing. For tomosynthesis, as shown in the top portion of FIG. 12B, x-ray source array 948, or movable source 949, may be used to form a set 470 of images, with one image 952 corresponding to each source 942 of array 948, or each position of source 949. Using this energization pattern for fixed sources 942, a tomosynthesis image may be generated without requiring movement of the x-ray sources of array 948 and detector relative to the imaged subject. Using movable one or more sources 949, a tomosynthesis image may be generated with minimal number of sources. Depth image reconstruction techniques then generate the depth image using set 470 of 2-D images. For fluoroscopy, as shown in the bottom portion of FIG. 12B, a single 2-D image may be repeatedly acquired, as represented by an image 952 that corresponds to image 952f in set 470. Using this mapping, it can readily be seen how later acquisition of a fluoroscopy image may serve to help update the depth image content obtained earlier. Significantly, the source-detector spatial relationship may be the same when image 952f is initially obtained as part of tomosynthesis set 470 and when the image from source 942f is later obtained for fluoroscopy.

According to an embodiment of the present disclosure, images 952 that are repeatedly obtained for fluoroscopy, using the same x-ray source 942, may be compared against earlier images obtained and used for tomosynthesis to determine whether or not the reconstructed depth image content is still accurate or needs to be updated. When image analysis shows, for example, that the tomosynthesis depth image that was obtained earlier might be misleading, a precautionary message may be displayed with the tomosynthesis depth image, indicating significant changes in image content. In this way, the results of fluoroscopy imaging may serve as a check on the overall accuracy of tomosynthesis reconstruction and depth information that is provided. For example, a tomosynthesis image taken earlier may show a catheter at a particular position. As catheter motion progresses, the tomosynthesis image becomes less accurate, and may even be misleading. Comparison of fluoroscopic images obtained from one of the same x-ray source positions that were used for the tomosynthesis reconstruction may help to indicate when the tomosynthesis information is no longer accurate, so that either a new reconstruction is needed or some precautionary message posted when the depth image displays. Any of a number of image processing methods that detect change in a feature or movement of position of a feature may be applied in order to check on whether or not depth image update is needed.

The number of most recently captured images for tomosynthesis imaging may be a one-time selectable number that remains constant during the operation of the imaging system. Display 442 (FIGS. 4A-4B) may be used to show the fluoroscopy image alongside the tomosynthesis image or to switch display modes between fluoroscopy and tomosynthesis.

Sequencing of X-Ray Sources

Figure 12C:
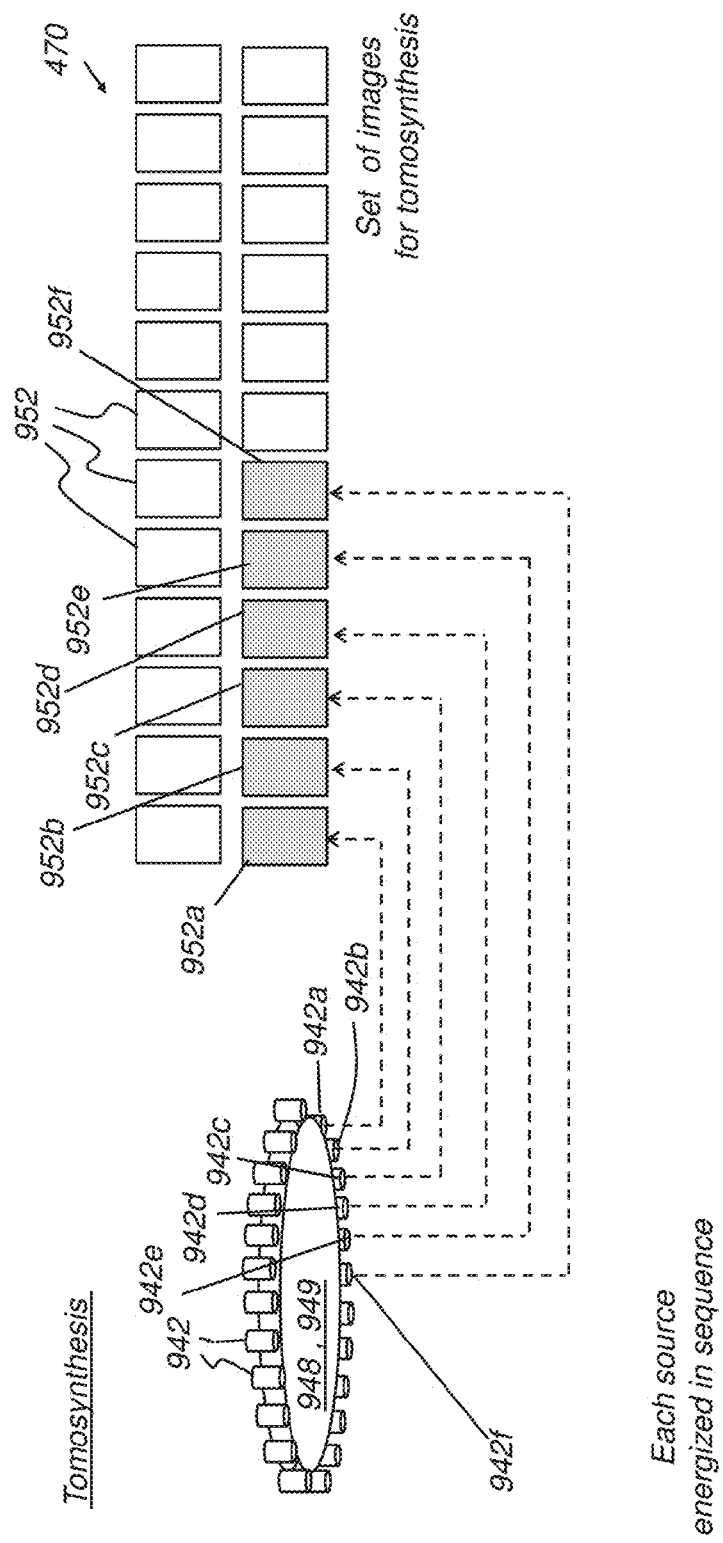
FIG. 12C is a schematic diagram that shows generation of a first tomosynthesis image using a subset of x-ray source positions.
Figure 12D:
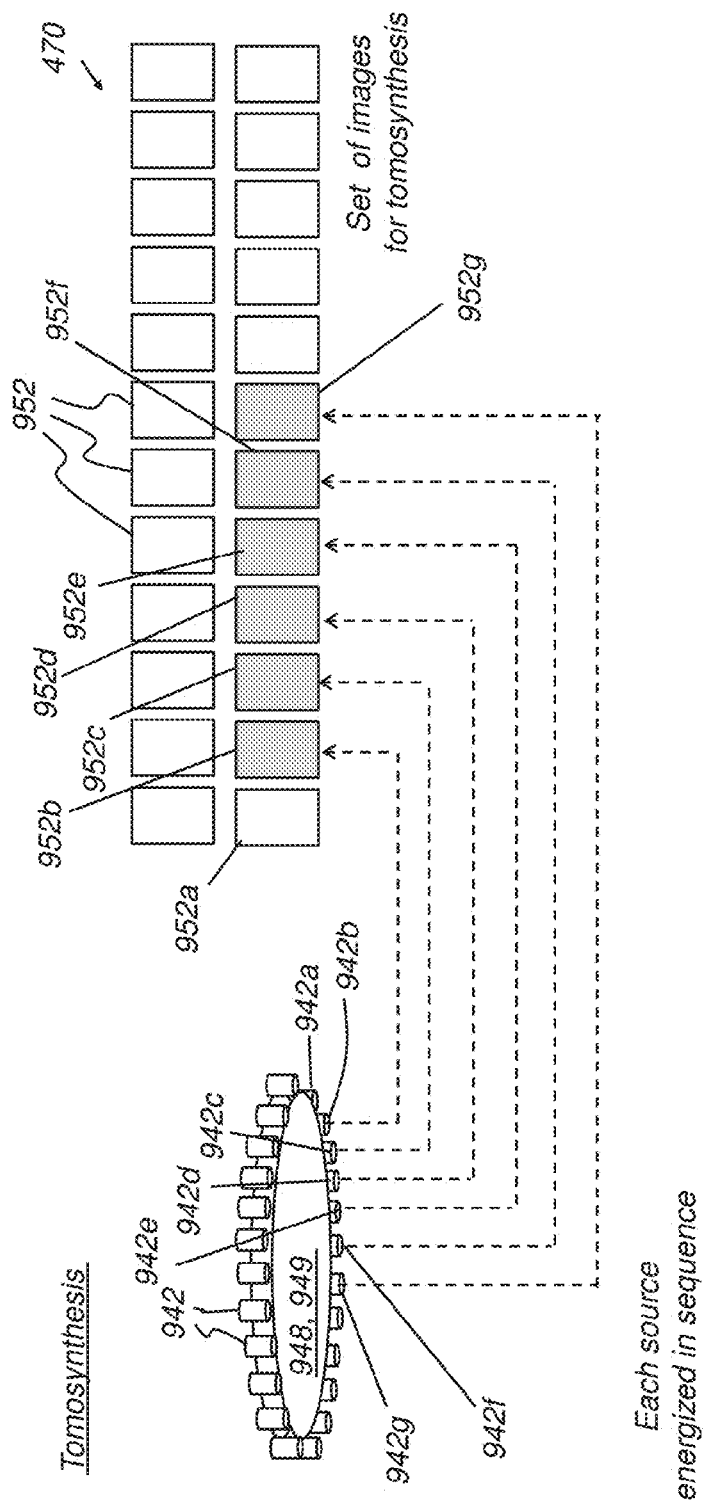
FIG. 12D is a schematic diagram that shows generation of a second tomosynthesis image.

When used for tomosynthesis imaging, different proper subsets of x-ray source array 948, or different positions of one or more movable sources 949 may be used for successive tomosynthesis reconstructions, as shown in the example of FIGS. 12C and 12D. In FIG. 12C, a first subset of x-ray sources {942a, 942b, 942c, 942d, 942e, and 942f} or movable x-ray source 949 in equivalent positions, may be used to generate a corresponding first subset of images {952a, 952b, 952c, 952d, 952e, and 952f} that may then be used to reconstruct and display a first tomosynthesis image. Similarly, a second subset of x-ray sources {942b, 942c, 942d, 942e, 942f, and 942g} may be used to generate a corresponding second subset of images {952b, 952c, 952d, 952e, 952f, and 952g} to reconstruct and display a second tomosynthesis image having slightly different depth content.

Figure 13A:
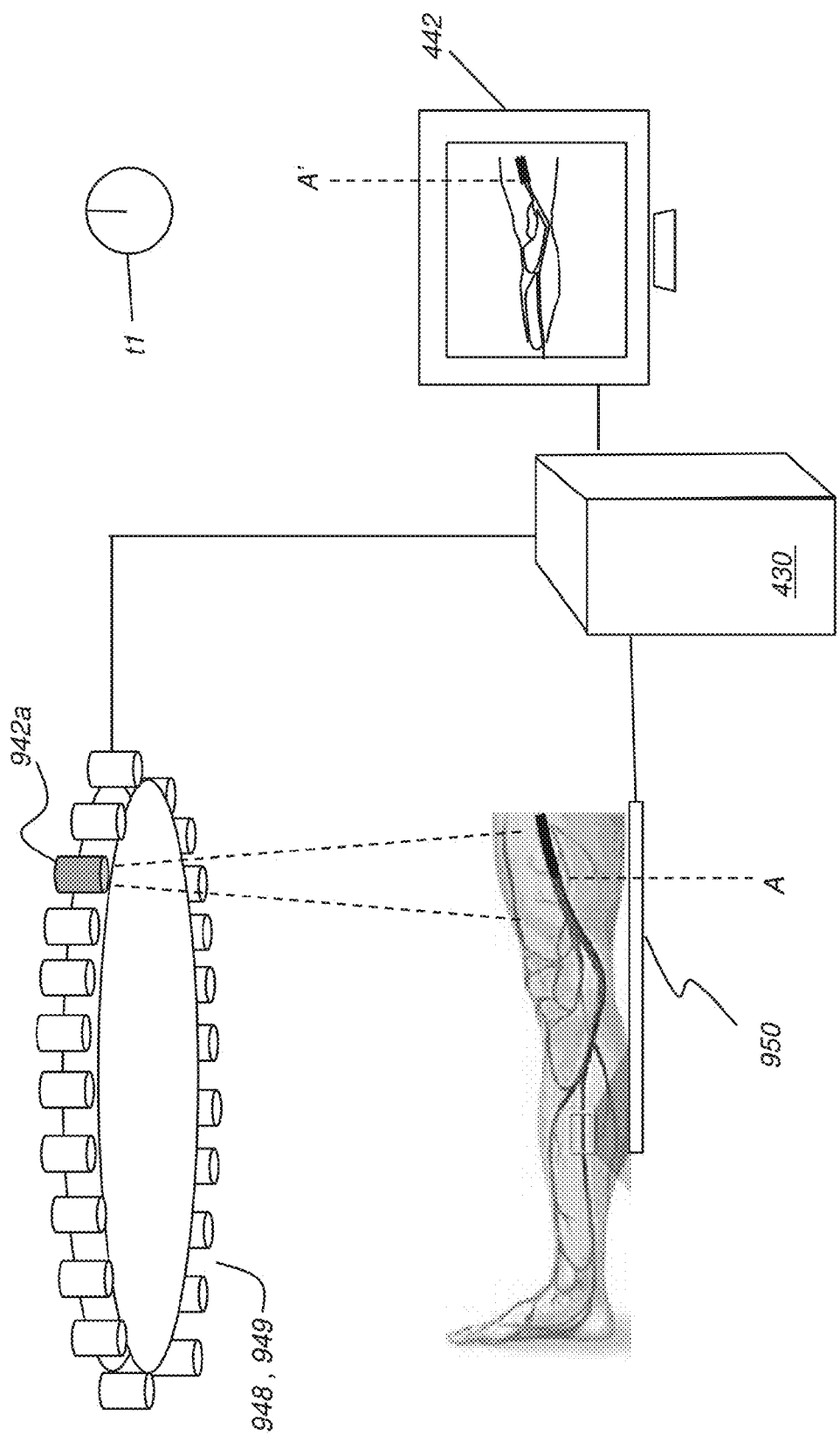
FIGS. 13A, 13B, and 13C are schematic diagrams that show use of an imaging apparatus for tracking a progressive procedure at different stages of a process.
Figure 13B:
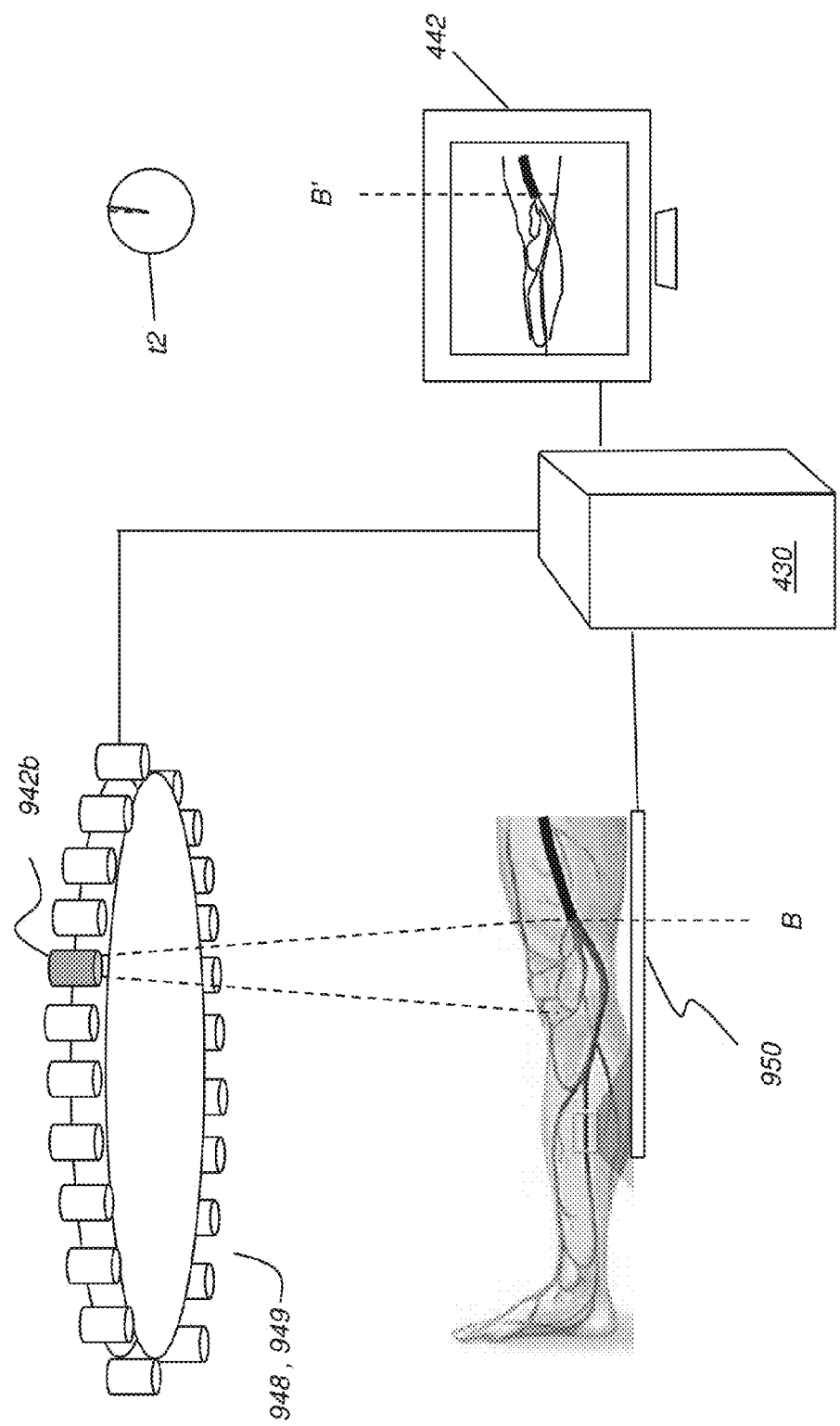
Figure 13C:
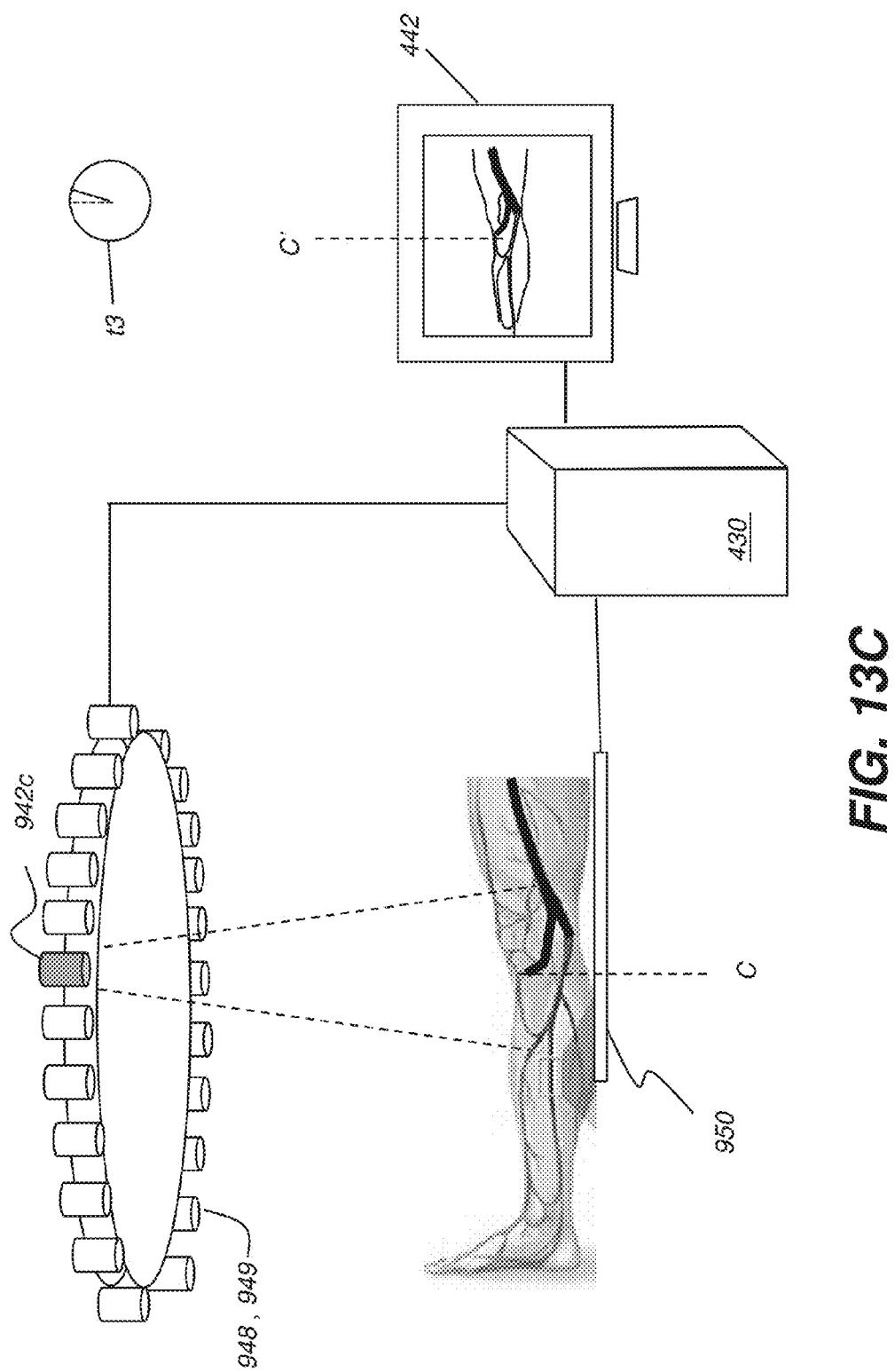

Alternatively, when using source array 948 with sources 942 that are capable of rapid switching, or one or more movable sources 949, a number of source excitation or firing sequencing arrangements may be used for fluoroscopic imaging, including sequencing in a pattern that automatically adjusts according to movement tracking, such as for tracking a catheter or a contrast agent traveling through a vein or artery or progressing through some other body cavity, for example. Referring to FIGS. 13A, 13B, and 13C, source array 948, or one or more movable sources 949, is configured for a circular or elliptical operation. At a time t1 in FIG. 13A, with a catheter as far as position A, a source at position 942a may be energized and detector 950 acquires image data for an imaging region with corresponding position A' shown on display 442. At a different time t2 in FIG. 13B, such as immediately following time t1, a source at position 942b may be energized and detector 950 acquires image data with the catheter extended to an imaging region at position B. The corresponding image shows catheter extension to position B'. At a later time t3 in FIG. 13C, such as immediately following time t2, a source at position 942c may be energized and detector 950 acquires image data with the catheter extended to an imaging region near position C. The corresponding image shows catheter extension to position C'. The rate at which the different x-ray source positions 942 are achieved, sequentially from one to the next, may be predetermined based on the type of procedure or may be based on tracking the progress of a particular procedure, so that detection of progress or of particular events may be used to control the pattern or position of the x-ray source or sources at a firing time t.

According to an alternate embodiment of the present disclosure, more than one x-ray source may be used for obtaining fluoroscopy images, with only one x-ray source energized at a time. Thus, for example, two adjacent or separated x-ray sources 942 in array 948 of FIGS. 9A-9C are alternately energized in a repeated cycle, thus reducing the heat load on any single source. Three or more x-ray sources could alternately be energized in this way for obtaining fluoroscopic image content.

Figure 14:
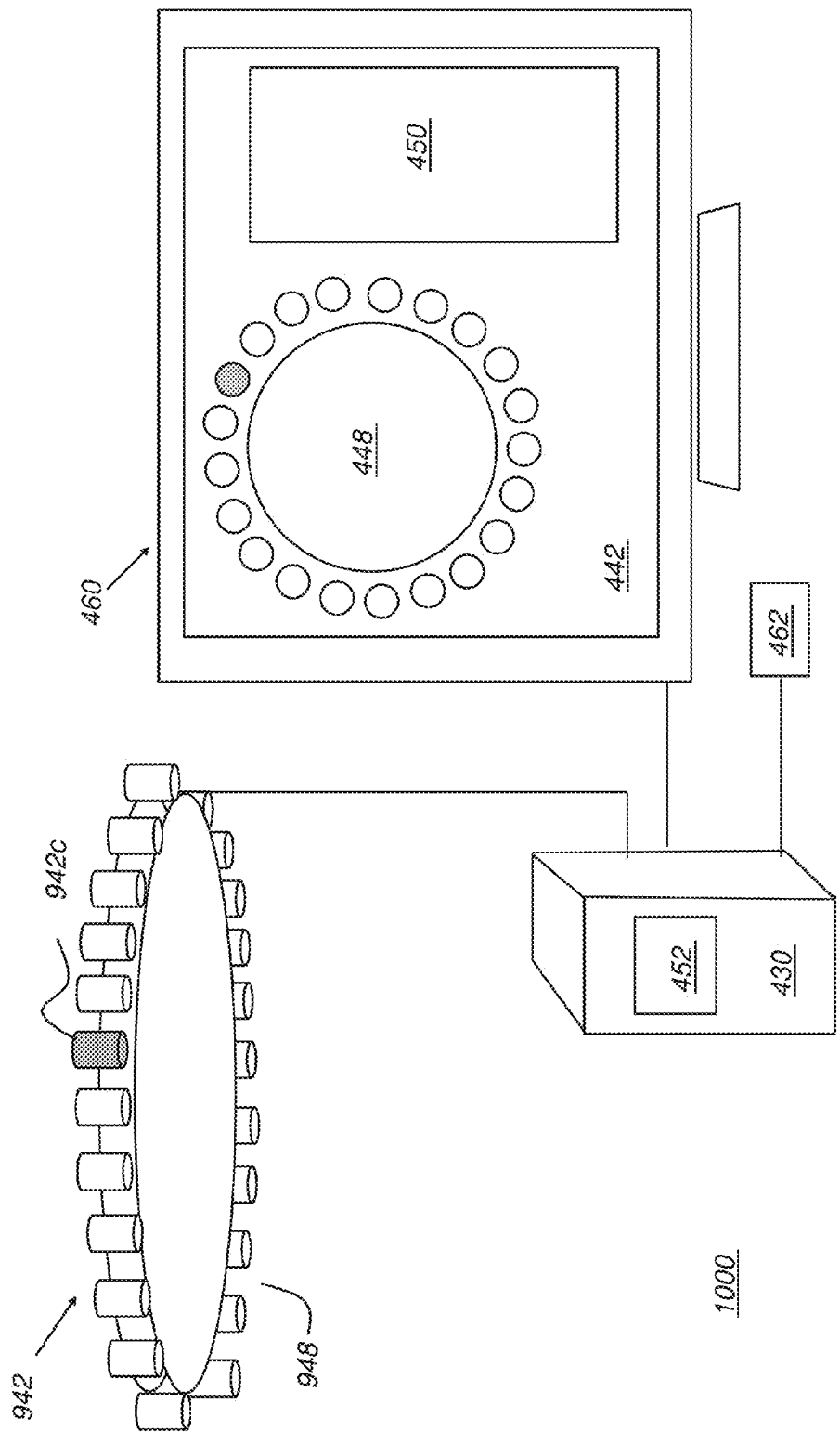
FIG. 14 is a diagram that shows a radiography apparatus with an operator interface for setting up and monitoring an energization sequence for an array of radiation sources.

FIG. 14 shows an embodiment of a radiography apparatus 1000 that has source array 948 with sources 942 in an arrangement that may be essentially circular. An operator interface 460 provides a graphic 448 that represents the x-ray source arrangement and that may show which source 942 may be energized or scheduled to be energized as part of a stored pattern 452 that stores an exposure sequence for execution by apparatus 1000. The stored pattern may be used for tomosynthesis imaging or for fluoroscopic imaging, during which an individual source 942 or two or more sources 942 may be repeatedly energized to provide fluoroscopic imaging along a predetermined path.

According to an embodiment of the present invention, an imaging sequence uses the central thermionic x-ray source 944 (FIG. 9A) for pulsed image or fluoroscopic imaging due to its heat dissipation characteristics and collimation ability, allowing suitable dose control. Peripherally distributed CNT or other distributed sources are then energized upon command as needed in order to generate images that help clarify the positional relationship of an interventional device such as a catheter to patient anatomy. This can be useful, for example, at a catheter tip location where branches or overlapping vessels or other features might otherwise obstruct the view if obtained using the central source 944. The ability to quickly acquire a projection image from an alternate angle, without physical repositioning of the source, can help to show features that would otherwise be obstructed or momentarily unclear. The thermionic source 944 may then be re-energized as the procedure continues. Switching between different sources may also be used to help balance the heat load within source array 948. One or more heat sensors 970 may be monitored and monitoring results used to adjust the pattern of source energization to control heat buildup in array 948.

According to an embodiment of the present invention, operator interface 460 of FIG. 14 allows user programming for setting up one or more exposure sequences as stored patterns 452. For this purpose, an instruction entry area 450 may be provided on display 442, allowing the user to schedule how long and in what order each source 942 is energized for a particular exposure sequence. Each x-ray source may be aimed at an imaging region of the subject to be imaged. According to an embodiment of the present disclosure, the stored schedule provides instructions for energizing each member of a subset of sources 942 in sequential order and for a programmed time interval. The subset may include each source 942 or may exclude one or more of the sources in the array 948. Thus, for example, a particular exposure sequence may be configured and stored for tracking a contrast agent that is expected to progress through a vein or other body cavity at a predictable rate.

In an alternative embodiment, the sequence order may be programmed and stored, but timing may not be stored; instead, the practitioner may be given the option to index through the programmed sequence during a procedure by using a switch 462 such as a foot pedal or by providing an audible signal or other prompt that instructs apparatus 1000 to advance to the next programmed step in sequence. In this way, the operator indexes through a predetermined sequence of steps that energize different x-ray sources at each step.

According to an alternate embodiment of the present disclosure, switch 462 may be an array of activation buttons, with each button configured to energize a single x-ray source 942. Display 442 may alternately be a touch screen for providing an activation-button interface to accept viewer instructions. In this way, exposure using multiple sources may be controlled by the practitioner so that the images obtained, whether for tomosynthesis or fluoroscopy, are at an optimal angle or set of angles and with a preferred exposure type for diagnostic assessment. It can be appreciated that a default timeout may also be used, so that operator instructions advance the sequence or extend the exposure time from specific sources in the array 948.

In one embodiment, the arranged or distributed low power source(s) may be an array 948 of carbon-nanotube x-ray sources that are disposed in a single vacuum chamber and are attached to a common fixture (FIGS. 8A-8D). In one embodiment, a plurality or all of the carbon nanotube cathodes of the x-ray sources 942 may be arranged in a circular formation such that their electron beams 852 are emitted in an outward direction in relation to a center of the circular arrangement. The emitted electron beams 852 may each be directed at one of a corresponding plurality of anodes all sharing a common electrical anode potential. Another anode embodiment may include a disc 850 with or without a central opening therethrough. For example, this disc anode embodiment may have a continuous, inward facing, annular beveled edge 851 (FIG. 8C) formed at a constant angle relative to an axis through the center of the circular arrangement (central axis), so that the electron beams 852 from the plurality of cathodes may impinge the beveled edge 851 of the anode disc 850 to generate x-ray emission at a suitable angle toward digital radiographic detector 950 (FIG. 9B). The disc anode 850 may rotate about the central axis so the focal points on the beveled edge 851 impacted by the electron beams 852 are distributed over the larger surface area, as compared to a stationary anode, to reduce damage (e.g., overheating, melting). In a similar fashion, the carbon nanotube cathodes may be disposed in a circular arrangement to emit an electron beam inward toward the central axis while the disc anode is formed such that its beveled edge faces outward, away from the central axis, at an angle suitable to direct x-rays toward the detector as explained herein.

Figure 15:
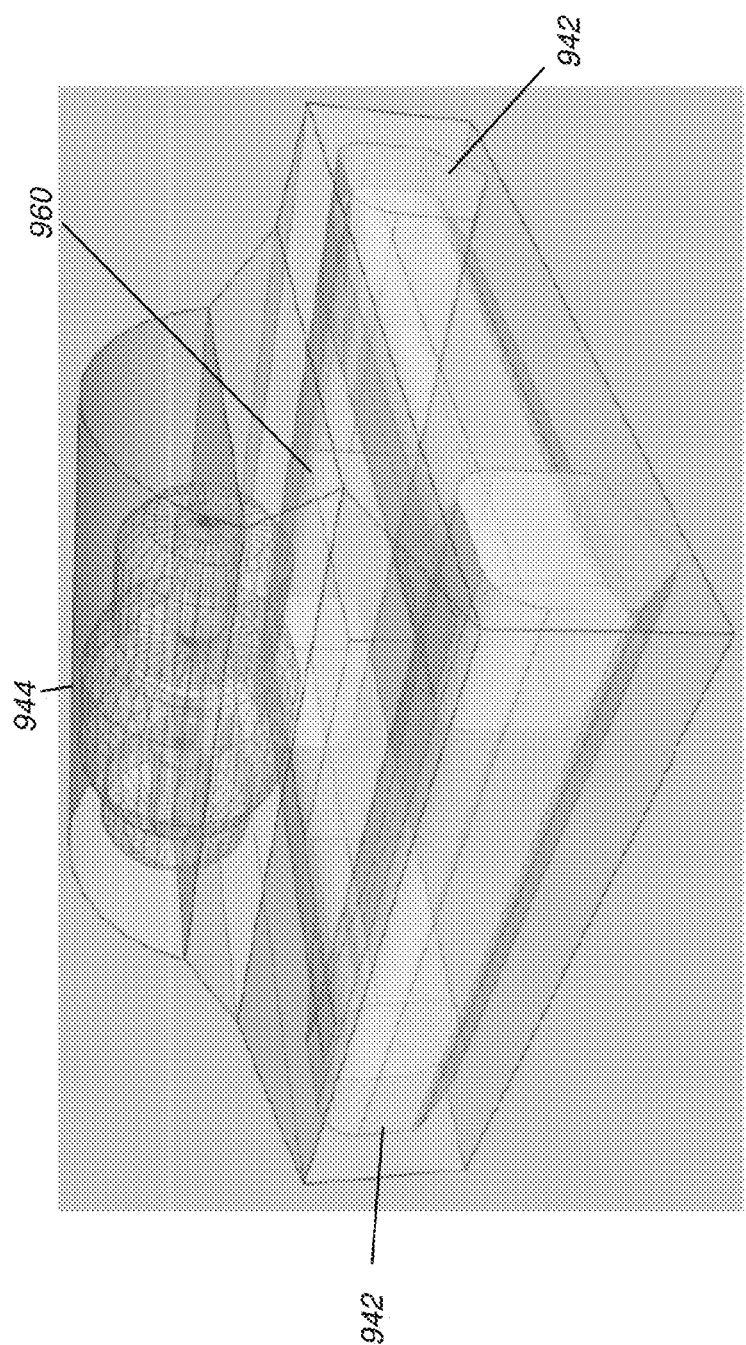
FIG. 15 is a perspective view that shows a shield and different types of radiation sources for combined tomosynthesis and general radiology.

As shown in FIG. 15, the x-ray hardware may include embodiments that use a central x-ray source 944 with a more traditional collimator 960. This central x-ray source may be used to capture traditional 2-D x-ray images.

Although a circular arrangement of distributed low power x-ray sources are shown here, other linear or non-linear arrangements or even prescribed geometric patterns (e.g., shapes, stars, diamonds, regular or irregular combinations, repeating) may be used with corresponding selectable array of collimation windows that may provide combined tomosynthesis and projection x-ray imaging.

Two different type of x-ray sources (i) general radiation source and (ii) distributed array of certain number of sources (e.g., lower power) may be included in a single x-ray source for a radiographic imaging system according to embodiments of the present disclosure.

One exemplary embodiment for the distributed array of sources may be a configuration that may include 30 or more distributed sources in a unit (e.g., unit array of distributed sources) at sides (e.g., each of 3-10 sides around a central area) to make an arrangement, which configuration may be separated and individually attached by unit array (or fastened together in a single entity) to a mechanical housing (e.g., tube head) of the imaging system. For certain exemplary embodiments, the unit arrays are not co-planar and may implement a different source-to-image distance (SID) for an imaging event or examination. For example, the unit arrays may be selectively co-planar, for example, two sides at different depths, three of four sides at different planes. Further, the (vertical, horizontal) distance between the unit arrays may be the same or different (e.g., increasing). Alternatively, adjacent or opposite pairs of unit arrays may have equal SIDs or be co-planar. Such a variation in arrangement may allow for a fixed x-ray source arrangement to implement a greater range of subject distances.

Various arrangements of source array 948 are possible, including exemplary embodiments that provide source array 948 in movable sections, with each section having one or more x-ray sources 942 for example. This would allow repositioning of x-ray sources 942 to provide a certain amount of overlap to radiation beam paths or to alter the effective source-to-image distance (SID). For example, a chest x-ray examination may use a longer SID than a head x-ray examination and accordingly, movement (e.g., spatial re-positioning and/or rotation) of the unit arrays may allow multiple distances or SIDs to be implemented with a single aperture (e.g., fixed collimation, pinhole) for each distributed source. Collimation may be adjusted to compensate for beam changes with angle.

In one embodiment, additional collimation may be used with a collimator disposed at a distance closer (e.g., 6 inches-2 feet) to the detector to provide an outer limitation to the collimated beams of the distributed array of sources.

In one embodiment, the unit arrays may be attached, adjusted and/or removed without tools. In one embodiment, the unit arrays may be attached and/or rotated between two positions where a first position may be outside an area traversed by a central x-ray beam (e.g., general radiology beam) and a second position to cross or cover the area traversed by the central x-ray beam. The second position in such a configuration can reduce an angular disbursement of beams from the distributed array of sources.

In one embodiment, a plurality of unit arrays (e.g., 6-8 unit arrays) may be implemented to move between a small retracted configuration and unfold multiple times to form a prescribed linear or non-linear configuration (e.g., multiple straight lines of sources or unit arrays), which can extend in multiple directions from/around a central beam.

In one embodiment, a plurality of unit arrays (e.g., 6-8 unit arrays) may be implemented as individual straight lines sources, but configured to approximate a circle.

Exemplary system and/or method embodiments according to the present disclosure may be used for in-room radiographic imaging systems and/or portable tomosynthesis. Portable tomosynthesis imaging may be able to provide the sought information at the bedside without subjecting the patient to the risks of transport to radiology. For example, tomosynthesis imaging can supply the required information to diagnose patient conditions that are non-differentiable with standard projection x-ray imaging such as chest x-rays.

According to an embodiment of the present invention, fluoroscopy may be effected using two or more adjacent x-ray sources, sharing the heat load that may be generated by repeated energization. Various alternating patterns are used, including using a subset of two or three x-ray sources that are adjacently disposed in the source array and not employing a sequence that energizes each x-ray source in the subset an equal number of times and wherein no x-ray source may be energized twice in sequence.

Digital Radiography (DR) Detector

The x-ray detector may be a digital x-ray detector with signal to noise ratio performance at low exposure to allow readout of the exposure sequences. According to an embodiment of the present disclosure, a DR detector for fluoroscopic imaging has a very high frame rate. For example, the x-ray detector may have a frame rate of about 30-60 frames per second; however, lower rates can still be usable. The DR detector should have excellent signal to noise ratio performance at low exposure to allow rapid readout of the rapid exposure sequences. According to an embodiment of the present disclosure, the digital detector employs sensors of complementary metal-oxide semiconductor (CMOS) technology.

The DR detector may be independent from the x-ray source array, mechanically de-coupled from the x-ray sources so that it can be positioned separately. The DR detector may be not movable from its fixed position during tomosynthesis or fluoroscopic imaging. This arrangement allows stereo images to be obtained from any of a number of different view angles, and allows the angular relationship of images to be dictated by the source array arrangement and source-to-image distance (SID), rather than being fixed, such as may be required with C-arm arrangements. The x-ray sources may be moved during a procedure to allow improved visibility.

Image Processor

The image processing logic must be capable of rapid spatial frequency processing. Lag time between image acquisition, processing, and data transmission must be reduced to low levels, so that response and refresh time of the DR detector and associated components may be as low as possible.

Figure 16:
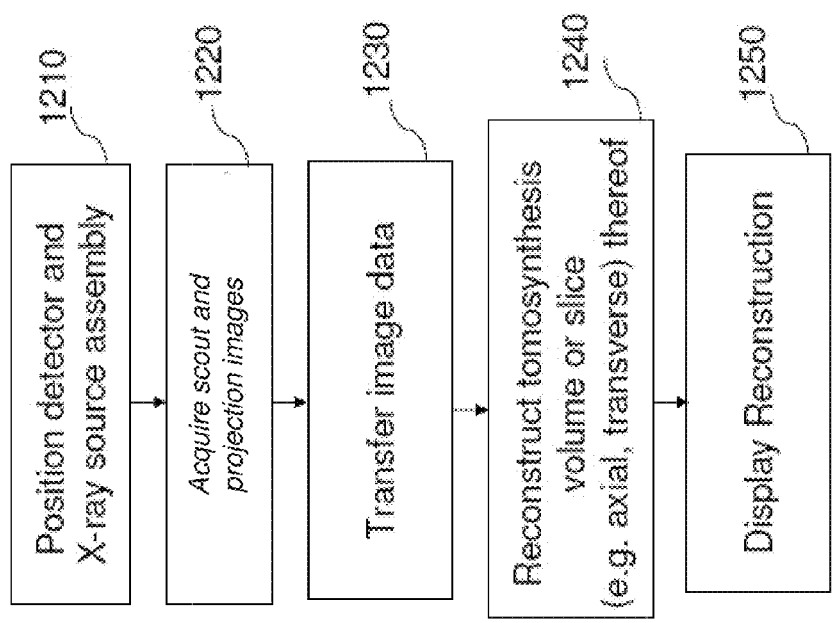
FIG. 16 is a logic flow diagram that shows an exemplary method of operating exemplary mobile radiographic imaging systems for acquiring projections images and generating the reconstruction of three-dimensional tomosynthesis images.

The flow chart of FIG. 16 shows an exemplary method for acquiring projection images and reconstruction of three-dimensional tomosynthesis images, according to an embodiment of the present disclosure. The method described may use embodiments of mobile radiography apparatus shown in FIG. 5, for example. Methods for image capture, processing, and presentation given in the present disclosure may be applied to other mobile or stationary imaging apparatus, without limitation to a particular type of system.

As shown in FIG. 16, in a positioning step 1210, the detector and x-ray source array may be positioned. For example, the x-ray source may be moved to its initial position and the detector may be positioned such that the patient P may be interposed between the detector and x-ray source.

For an embodiment of exemplary mobile radiographic/tomosynthesis unit 900 of FIG. 5, the initial x-ray source array position may be set by the location of transport frame 920 and the support column 930 to which the source array may be coupled. The height, extent and rotation positioning of first section 930a and second section 930b of support column 930, or positioning elements that are themselves connected to support column 930, may be used to position the x-ray source array 940 to the initial desired location with respect to the patient.

Following positioning step 1210 in FIG. 16, an image acquisition step 1220 optionally acquires one or more scout images, then acquires a series of projection images at different x-ray source positions. Each of the projection images may be acquired while corresponding individual x-ray sources are triggered. In one embodiment, the first radiographic x-ray source may operate as a central one of the distributed sources. In a transfer step 1230, the acquired projection image data may be received (e.g., transferred back from the detector to the system) by control and processing components of the system controller. The projection images may be displayed on display 910 and/or undergo a quality check (e.g., automated or by the operator) before being further processed. The projection image data may also be processed in transfer step 1230 to permit raw, partially-processed or fully-processed images or tomosynthesis slices to be stored (e.g., to support temporality at the detector) and/or sent to remote locations.

Continuing with the FIG. 16, sequence, tomosynthesis image reconstruction may be performed (e.g., real-time) using the acquired corrected projection image data in a reconstruction step 1240. Image reconstruction may use processes similar to those used for conventional tomosynthesis imaging. For example, as will be appreciated by those skilled in the art, back projection, filtered back projection, iterative reconstruction, or other known reconstruction techniques may be used. In one exemplary embodiment, a particular position of the source with respect to the detector may be determined by knowledge of the position of the x-ray source array and the detector based upon the values set by an operator, or automatically determined according to image capture timing or by using a grid alignment system to adjust the values or by a tethered connection to source and detector positioning circuitry, for example. The reconstructed volume may be provided on display 910 in a display step 1250.

The reconstructed volume may alternately undergo a quality check before display. In one embodiment, the reconstruction volume may be stored after the quality check (e.g., before display). Further, the display may be used to view underlying projection images or projection images generated by the system, or to view the tomosynthesis reconstructions themselves. Further, underlying data and/or reconstructed tomosynthesis images may be transmitted to a remote system for additional analysis or display.

Figure 17:
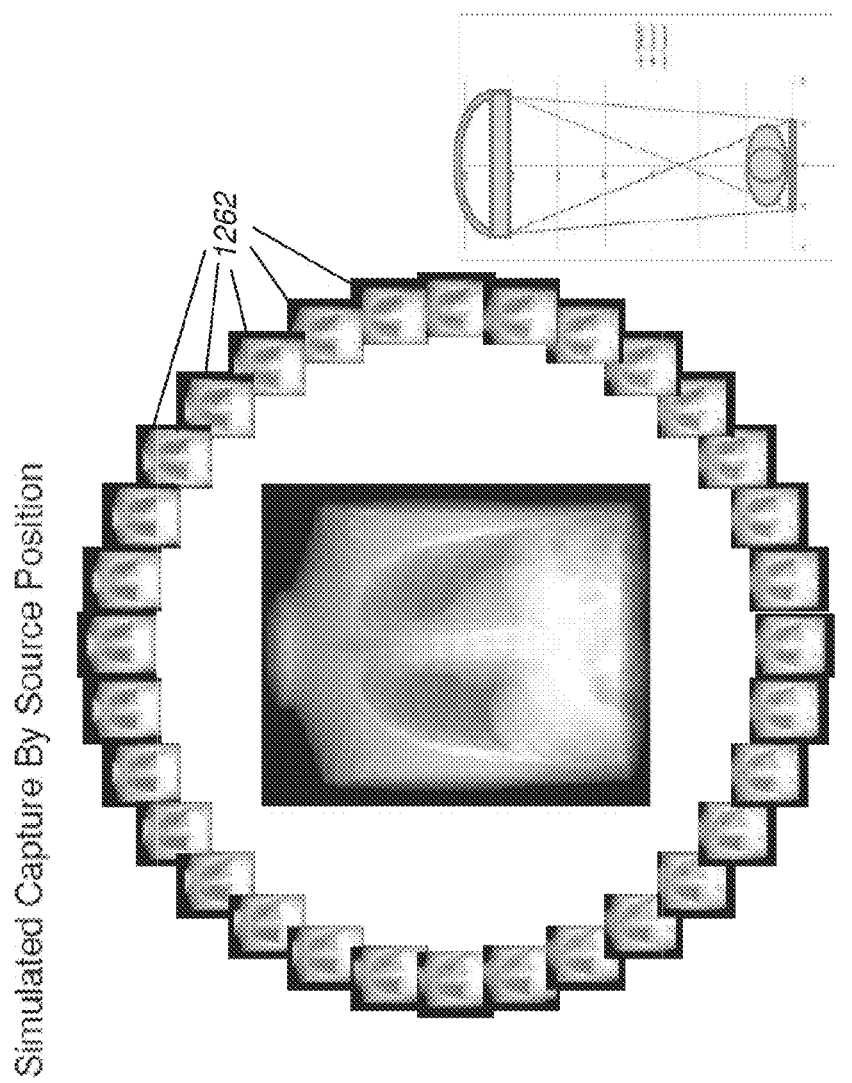
FIG. 17 shows simulations of exemplary projection images obtained using x-rays from each x-ray source position.

FIG. 17 shows simulations of exemplary projection images 1262 for tomosynthesis obtained using x-rays from each source position of a circular source array 948. In practice, a smaller number of images than those shown may be all that is needed for tomosynthesis reconstruction.

Figure 18:
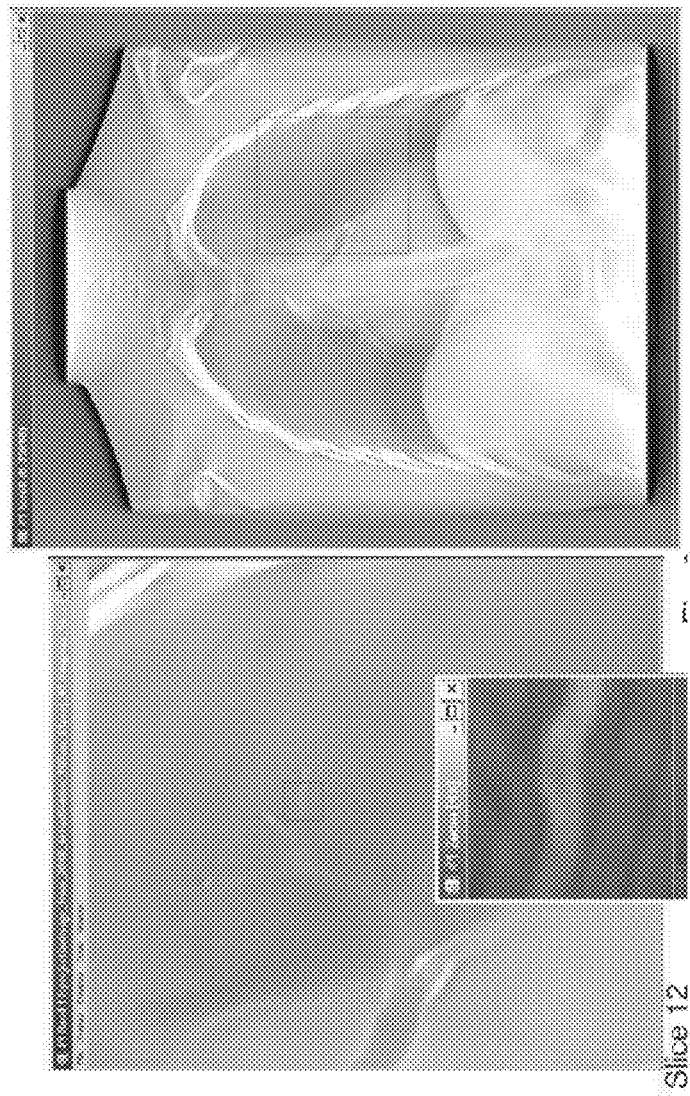
FIG. 18 shows a tomosynthesis reconstruction image according to an embodiment of the present disclosure.

FIG. 18 shows a tomosynthesis reconstruction image 1300 according to an embodiment of the present disclosure.

The tomosynthesis image 1300 displays to the practitioner as a 2-D slice extracted from the volume data.

One embodiment utilizes a computer program with stored instructions that perform on image data that may be accessed from an electronic memory. As can be appreciated by those skilled in the image processing arts, a computer program of an embodiment of the present invention may be utilized by a suitable, general-purpose computer system, such as a personal computer or workstation that acts as an image processor. However, many other types of computer systems may be used to execute computer programs of the present invention, including an arrangement of networked processors, for example. The computer program for performing methods of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing methods of the present invention may also be stored on computer readable storage medium that may be connected to the image processor by way of the internet or other network or communication medium. Those skilled in the art will further readily recognize that the equivalent of such a computer program product may also be constructed in hardware.

It is noted that the term "memory", equivalent to "computer-accessible memory" in the context of the present disclosure, may refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that may be used as a temporary buffer or workspace by a microprocessor or other control logic processor device. Display data, for example, may be typically stored in a temporary storage buffer that may be directly associated with a display device and may be periodically refreshed as needed in order to provide displayed data. This temporary storage buffer may also be considered to be a memory, as the term is used in the present disclosure. Memory may be also used as the data workspace for executing and storing intermediate and final results of calculations and other processing. Computer-accessible memory may be volatile, non-volatile, or a hybrid combination of volatile and non-volatile types.

It is understood that computer program products of the present invention may make use of various image manipulation algorithms and processes that are well known. It will be further understood that the computer program product embodiments of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program products of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications may be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An imaging system comprising:
   an x-ray assembly aimed at an imaging region of a patient, the x-ray assembly configured to be energizable to emit ionizing radiation from one or multiple different spatial positions toward the imaging region;
   control hardware configured to energize the x-ray assembly to emit ionizing radiation at predetermined times from each of the one or more of the spatial positions; and
   a digital x-ray detector in digital communication with the imaging system, the digital x-ray detector to capture a radiographic image of the imaging region of the patient in response to energizing the x-ray assembly,
   wherein a first mode of operation of the imaging system comprises energizing the x-ray assembly to emit ionizing radiation from a first spatial position toward the imaging region of the patient,
   a second mode of operation of the imaging system comprises energizing the x-ray assembly to emit ionizing radiation multiple times each from a different one of the spatial positions, and
   wherein the control hardware is configured to switch the imaging system between the first and second modes of operation in response to an event occurring in the imaging region of the patient as captured in a radiographic image.

2. The system of claim 1, wherein the detector is configured to capture and store a plurality of radiographic images of the imaging region of the patient in response to operating the imaging system in the second mode of operation, and wherein the captured plurality of images are used to reconstruct a tomographic image of the imaging region of the patient.

3. The system of claim 2, wherein one or more stored radiographic images of the imaging region of the patient captured in response to operating the imaging system in the first mode of operation are used together with the plurality of images captured in the second mode to reconstruct a tomographic image of the imaging region of the patient.

4. The system of claim 1, wherein the control hardware comprises non-transitory stored control program instructions operable to controllably energize the x-ray assembly in a programmed firing sequence, and wherein the firing sequence defines the predetermined times and the one or more of the spatial positions.

5. The system of claim 4, wherein the control hardware further comprises:
   non-transitory stored control program instructions operable to controllably energize the x-ray assembly in a plurality of programmed firing sequences; and
   input means for receiving an input from an operator of the imaging system to activate a selected one of the plurality of programmed firing sequences.

6. The system of claim 1, wherein the control hardware comprises an input means for receiving an input from an operator of the imaging system to switch the imaging system between the first and second modes of operation.

7. The system of claim 1, wherein the control hardware comprises an input means for receiving an input from an operator of the imaging system to select the predetermined times and the one or more of the spatial positions.

8. The system of claim 1, wherein a third mode of operation comprises energizing the x-ray assembly one or more times from the first spatial position toward the imaging region of the patient, energizing the x-ray assembly one or more times from a second spatial position toward the imaging region of the patient, alternating between energizing the x-ray assembly one or more times from the first spatial position and from the second spatial position toward the imaging region of the patient, or a combination thereof.

9. The system of claim 1, wherein the x-ray assembly comprises a plurality of x-ray sources in a fixed spatial arrangement in relation to one another, and wherein each of the plurality of fixed x-ray sources correspond to one of the different spatial positions.

10. The system of claim 9, further comprising a fixture to secure the plurality of x-ray sources all in a fixed first position in relation to the imaging region of the patient, wherein the fixture is repositionable to secure the plurality of x-ray sources all in a fixed second position in relation to the imaging region of the patient.

11. The system of claim 9, wherein the x-ray sources comprise a plurality of cathodes arranged along an arc to each emit an electron beam radially outward from a center of the arc toward a common substantially circular anode, the anode comprising a rotating disc having a continuous anode surface receiving the electron beams and emitting x-rays in response thereto.

12. The system of claim 1, wherein the x-ray assembly comprises a movable x-ray source, the movable x-ray source configured to be movable to each of the different spatial positions.

13. The system of claim 12, wherein the x-ray assembly comprises two or more movable x-ray sources, the movable x-ray sources configured such that at least one is movable to the different spatial positions.

14. The system of claim 1, wherein the control hardware comprises non-transitory stored control program instructions operable to switch the imaging system between the first and second modes in response to the imaging system detecting the event occurring in the imaging region of the patient.

15. The system of claim 14, wherein the event occurring in the imaging region of the patient is automatically detectable by the imaging system in the radiographic image of the imaging region.

16. The system of claim 15, wherein the event occurring in the imaging region of the patient is automatically detected by the imaging system operating in the first mode.

17. The system of claim 16, wherein the control program switches an operating mode of the imaging system from the first mode to the second mode automatically in response to the imaging system automatically detecting the event occurring in the imaging region of the patient.

18. The system of claim 17, wherein the event occurring in the imaging region of the patient occurs in a body cavity or fluid vessel of the patient.

19. The system of claim 18, wherein the event occurring in the imaging region of the patient comprises a radio opaque object or a radiographically detectible fluid moving through the body cavity or fluid vessel of the patient.

20. The system of claim 1, wherein the event occurring in the imaging region of the patient comprises a radio opaque object or a radiographically detectible fluid moving through a body cavity or fluid vessel of the patient.

21. An imaging system comprising:
an x-ray assembly aimed at an imaging region of a patient, the x-ray assembly configured to be energizable to emit ionizing radiation from one or multiple different spatial positions toward the imaging region;
control hardware configured to energize the x-ray assembly to emit ionizing radiation at predetermined times from each of the one or multiple different spatial positions; and
wherein a first mode of operation of the imaging system comprises energizing the x-ray assembly to emit ionizing radiation from a first spatial position toward the imaging region of the patient,
a second mode of operation of the imaging system comprises energizing the x-ray assembly to emit ionizing radiation multiple times each from a different one of the spatial positions, and
wherein the control hardware is configured to automatically select the predetermined times and multiple spatial positions to energize the x-ray assembly in response to an event occurring in the imaging region of the patient as captured in a radiographic image.

* * * * *